(12) United States Patent
Cohen et al.

(10) Patent No.: US 8,170,665 B2
(45) Date of Patent: May 1, 2012

(54) QUANTUM DOT LABELED STEM CELLS FOR USE IN PROVIDING PACEMAKER FUNCTION

(75) Inventors: Ira S. Cohen, Stony Brook, NY (US);
Amy B. Rosen, New York, NY (US);
Peter R. Brink, Setauket, NY (US);
Glenn Gaudette, Holden, MA (US);
Michael R. Rosen, New York, NY (US);
Richard B. Robinson, Cresskill, NJ (US)

(73) Assignees: The Trustees of Columbia University in the City of New York, New York, NY (US); The Research Foundation of State University of New York, Albany, NY (US)

( * ) Notice: Subject to any disclaimer, the term of this patent is extended or adjusted under 35 U.S.C. 154(b) by 884 days.

(21) Appl. No.: 12/077,970

(22) Filed: Mar. 21, 2008

(65) Prior Publication Data
US 2009/0062876 A1 Mar. 5, 2009

Related U.S. Application Data

(60) Provisional application No. 60/919,627, filed on Mar. 23, 2007, provisional application No. 60/936,873, filed on Jun. 22, 2007.

(51) Int. Cl.
*A61N 1/00* (2006.01)
(52) U.S. Cl. ............................................. 607/9
(58) Field of Classification Search ...... 607/9; 436/524; 435/41
See application file for complete search history.

(56) References Cited

U.S. PATENT DOCUMENTS
6,855,551 B2 2/2005 Bawendi et al.
(Continued)

FOREIGN PATENT DOCUMENTS
WO 2008118410 A2 10/2008

OTHER PUBLICATIONS
Ballou et al. Noninvasive Imaging of Quantum Dots in Mice. Bioconjugate Chem., 2004, vol. 15, 79-86.*

(Continued)

*Primary Examiner* — George Manuel
(74) *Attorney, Agent, or Firm* — Evans & Molinelli PLLC; Eugene J. Molinelli

(57) ABSTRACT

The present invention provides methods and compositions relating to the labeling of target cells with nanometer scale fluorescent semiconductors referred to as quantum dots (QDs). Specifically, a delivery system is disclosed based on the use of negatively charged QDs for delivery of a tracking fluorescent signal into the cytosol of target cells via a passive endocytosis-mediated delivery process. In a specific embodiment of the invention the target cell is a stem cell, preferably a mesenchymal stem cell (MSC). Such labeled MSCs provide a means for tracking the distribution and fate of MSCs that have been genetically engineered to express, for example, a hyperpolarization-activated cyclic nucleotide-gated ("HCN") channel and administered to a subject to create a biological pacemaker. The invention is based on the discovery that MSCs can be tracked in vitro for up to at least 6 weeks. Additionally, QDs delivered in vivo can be tracked for up to at least 8 weeks, thereby permitting for the first time, the complete 3-D reconstruction of the locations of all MSCs following administration into a host.

31 Claims, 8 Drawing Sheets

U.S. PATENT DOCUMENTS

Figure 1A:
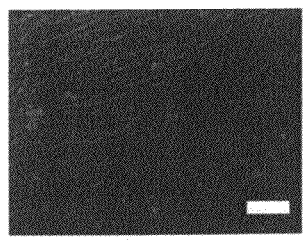

| | | | |
|---|---|---|---|
| 7,129,058 B2* | 10/2006 | Yamashita | 435/41 |
| 2004/0254134 A1 | 12/2004 | Marban et al. | |
| 2006/0078490 A1 | 4/2006 | Shih et al. | |
| 2006/0148104 A1* | 7/2006 | Marini et al. | 436/524 |
| 2006/0234298 A1 | 10/2006 | Chiu et al. | |
| 2007/0053886 A1 | 3/2007 | Rosen et al. | |
| 2007/0060815 A1 | 3/2007 | Martin et al. | |

OTHER PUBLICATIONS

Pittenger et al. Mesenchymal Stem Cells and Their Potential as Cardiac Therapeutics Circulation Res, 2005, vol. 95, pp. 9-20.*

Parak et al. Labelling of cells with quantum dots. Nanotechnology, 2005, vol. 16, pp. R9-R25.*

Frangioni et al. In Vivo Tracking of Stem Cells for Clinical Trials in Cardiovascular Disease. Circulation, 2004, vol. 110, pp. 3378-3384.*

ISA, "International Preliminiary Report on Patentability for Corresponding PCT application No. PCT/US2008/003843", Sep. 29, 2009, pp. 1-8, Publisher: WIPO.

ISA, "International Search Report and Written Opinion for Corresponding PCT application No. PCT/US08/03843", Sep. 10, 2008, pp. 1-10, Publisher: WIPO.

* cited by examiner

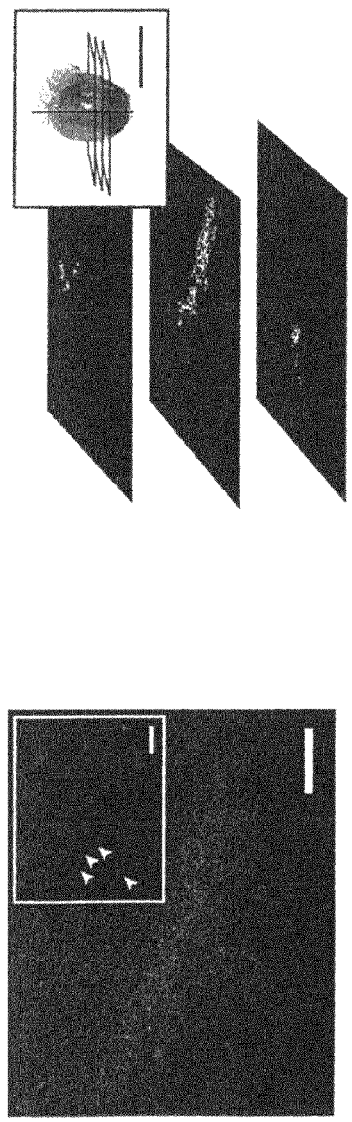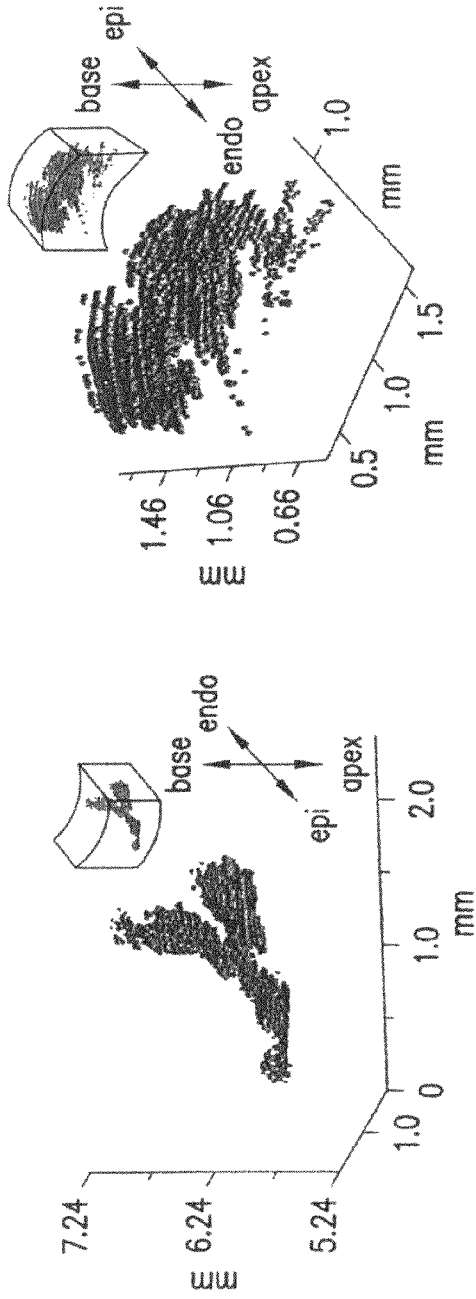
FIG.5A FIG.5B FIG.5C FIG.5D

QUANTUM DOT LABELED STEM CELLS FOR USE IN PROVIDING PACEMAKER FUNCTION

CROSS REFERENCE TO RELATED APPLICATIONS

This application claims priority to U.S. Application No. 60/919,627, filed Mar. 23, 2007, and 60/936,873 filed Jun. 22, 2007, which are incorporated herein by reference in their entirety.

This research was supported by USPHS-NHLBI grants HL-28958 and HL-67101. The United States Government may have rights in this invention.

1. INTRODUCTION

The present invention provides methods and compositions relating to the labeling of target cells with nanometer scale fluorescent semiconductors referred to as quantum dots (QDs). Specifically, a delivery system is disclosed based on the use of negatively charged QDs for delivery of a tracking fluorescent label into the cytosol of target cells via a passive endocytosis-mediated delivery process. In a specific embodiment of the invention the target cell is a stem cell, preferably a mesenchymal stem cell (MSC). Such labeled MSCs provide a means for tracking the distribution and fate of MSCs that have been genetically engineered to express, for example, a hyperpolarization-activated cyclic nucleotide-gated ("HCN") channel and administered to a subject to create a biological pacemaker. The invention is based on the discovery that MSCs can be tracked in vitro for up to at least 6 weeks. Additionally, QDs delivered in vivo can be tracked for up to at least 8 weeks, thereby permitting for the first time, the complete 3-D reconstruction of the locations of all MSCs following administration into a host.

2. BACKGROUND OF INVENTION

2.1 Quantum Dots

Quantum dots (QDs) are semiconductor nanoparticles that were discovered in the early 1980's. QDs used for biological applications consist of a cadmium selenide or cadmium tellurium semiconductor core, a zinc sulfide inner shell and an outer polymer coating. The result is a water-soluble particle 13-15 nm in diameter.

Similar to organic fluorophores, QDs absorb photons of light of one wavelength and emit light of a different wavelength. Traditional fluorophores use absorbed energy to transfer electrons to excited states and energy is released in the form of fluorescent light when these electrons return to their resting states. When electrons move to different energy levels in QDs, they behave analogously, generating electron holes called excitons. The quantum system of excitons makes QD fluorescence much brighter and more photostable (less prone to photobleaching) than traditional fluorophores.

The energy state of an exciton dictates the wavelength of light emitted by a particular QD after excitation. QDs have a unique property known as tunability, wherein the physical size of the QD determines the wavelength of emitted light. Smaller dots emit blue fluorescent light and as the core size of the dots increases, emitted light becomes redder. Another important feature that distinguishes QDs from conventional fluorescent dyes is the large distance between the wavelength of excitation and emission light. This energy difference, known as the Stokes' shift, means that QDs can be excited by ultraviolet light at a wavelength much lower than the peak emission wavelength. Thus, QDs can be excited by any wavelength lower than its emission wavelength. Therefore, particles are excited and emitted light is collected in a very efficient manner.

The first biological uses for QDs were reported in 1998. Since then, a number of novel applications for QDs have been described. For example, Dubertret, et al (Science, 2002, 298: 1759-62) reported the encapsulation of QDs within micelle-forming hydrophilic polymer-grafted lipids and delivery via microinjection into single cells of Xenopus embryos. Major findings from this study were that only the originally injected cells and their progeny retained QDs, labeled cells showed no signs of toxicity, all embryonic cell types were able to arise from labeled cells, the QD fluorescence was detectable above high levels of auto-fluorescence and most importantly, QDs were biocompatible. However, this group also reported that intracellular QDs tend to aggregate around the nucleus over time (Science, 2002, 298:1759-62). A similar published study demonstrated the use of QDs as lineage tracers by microinjecting into single cells of zebrafish embryos. Here it was shown that the dots were nontoxic, retained their emission spectra regardless of microenvironment, could be induced to avoid perinuclear aggregation by surface modification with streptavidin, did not pass through gap junctions, and could be imaged in aldehyde-fixed tissue (Rieger et al., Dev. Dyn 2005, 234:670-81). Both of these studies showed that the presence of intracellular QDs did not affect proliferation or differentiation of cells nor did they preclude formation of a fully-grown organism.

Two later published articles demonstrated that populations of cells could be labeled with QDs. Jaiswal, et al, reported a receptor-mediated and generalizable endocytotic method for introducing QDs into the intracellular space for live cell imaging (Nat Biotechnol 2003, 21:47-51). Unfortunately, the reported images revealed the problem of perinuclear aggregation. Wu, et al, highlighted the ability of QDs for use in multiplex immunostaining of fixed cells (Wu et al., 2003, Nat Biotechnol 21:41-6). Others have compared loading populations of cells via commonly used approaches including receptor-mediated transfection with a host of proteins (Hanaki et al., Biochem Biophys Res Commun 2003, 302:496-501; Silver et al., Nano Letters 2005, 5:1445-1449; Zhang et al., J. Biomediacal Materials Research Part B: Applied Biomaterials, 2005, 76B:161-168: So et al., Nat Biotechnol 2006, 24:339-43), lipid-mediated transfection and electroporation (Derfus et al., Advanced Materials 2004, 16:961). While both lipid-mediated transfection and electroporation have the added problem of causing some degree of cell death, none of the approaches reported to date have uniformly and efficiently loaded populations of cells and all have resulted in perinuclear aggregation.

2.2 Stem Cell Based Therapies

The past decade has seen rapid advances in the use of embryonic and adult stem cells for tissue regeneration and repair in the heart[1-3]. These cells are believed to have the potential to differentiate into mature cardiac cells or promote native repair through angiogenesis, recruitment of host stem cells or induction of myocytes into the cell cycle[2, 4-6]. Additionally, stem cells genetically engineered to express hyperpolarization-activated cyclic nucleotide-gated (HCN) genes have been utilized to create biological pacemakers. However, one drawback associated with such studies is the inability to adequately track delivered stem cells with sufficient resolution in large animals. The ability to account for exogenous stem cells after delivery to animal models is important not only for determining the overall efficacy of intended treatments, but also to rule out potentially dangerous side effects.

Traditional tracking agents such as GFP or fluorescent dyes fail to illuminate delivered cells above high levels of autofluorescence in the heart. Secondary staining as used to detect lacZ or amplify GFP generates false positives and would also involve painstaking efforts to identify 100% of the exogenous cells in hundreds of tissue sections. More recently, cells have been labeled with inorganic particles for detection by MRI or PET, but these imaging approaches can resolve no fewer than thousands of cells.

The present invention provides a novel approach to tracking cells, administered to a subject, using intracellular quantum dots (QDs). The invention is based on the demonstration that QD labeled hMSCs can be easily identified in histologic sections to determine their location for at least 8 weeks following delivery in vivo. Further, this approach has been used for the first time to generate a complete three-dimensional reconstruction of an in vivo stem cell "node."

3. SUMMARY OF THE INVENTION

The present invention provides a delivery system for transfer of QDs into the cytosol of target cells. Specifically, negatively charged QDs are described for use in delivering a tracking fluorescent label into the cytosol of the desired target cells. The methods of the invention are based on the surprising discovery that negatively charged QDs are efficiently delivered into the cytosol of a target cell through a passive endocytosis-mediated delivery system. A number of benefits are found to be associated with the use of the delivery system of the invention including ability to image without autofluorescence, lack of perinuclear aggregation of the dots, ease of use, reliability and reproducibility, as well as a lack of cellular toxicity. Additionally, the intracellular QDs do not interfere with cellular function and the labeled cells are capable of continued proliferation without loss of detectable label. Moreover, the labeled cells do not transfer label to adjacent cells.

The delivery system of the invention comprises contacting a target cell population with negatively charged QDs for a time sufficient to permit transfer of QDs into the cytosol of the target cell. In an embodiment of the invention the QDs emit light at wavelengths between about 525 nm and 800 nm. In a specific embodiment of the invention the target cell is a stem cell, preferably a MSC.

The compositions of the invention comprise labeled target cells that have taken up QDs through use of the delivery system of the invention. The QD-labeled cells of the invention lack perinuclear aggregation and show a uniform diffuse cytoplasmic labeling. In a preferred embodiment of the invention the labeled cells are stem cells, preferably MSCs. Also within the scope of the invention are QD-labeled cells that have been genetically engineered to express a desired protein of interest. For example, QD-labeled cells may be engineered to express HCN proteins, mutants and chimeras capable of providing biological pacemaker function.

A number of recently developed therapies are based on the administration of cells, such as stem cells, for treatment of a variety of different disorders. For example, the use of stem cells engineered to express HCN proteins to provide biological pacemaker activity has been described. The methods and compositions of the present invention may be used, for example, for tracking MSC mediated cardiac repair in a subject, comprising administering to said subject an effective amount of QD-labeled MSCs expressing HCN genes and determining the anatomy of node formation, as well as identifying whether there is migration of the MSCs to other sites in the body. Such methods and compositions provide a means for studying the safety and efficacy of stem cell use to treat different cardiac disorders, including but not limited to cardiac rhythm disorders, disorders at the sino-atrial node and disorders of the atrioventricular node.

4. BRIEF DESCRIPTION OF THE FIGURES

FIG. 1. Quantum dots can be loaded uniformly into hMSCs by passive incubation. QD loading was achieved by receptor-mediated uptake or passive incubation with naked dots. Panels (a) and (b) show images of QD fluorescence (655-nm, red) with phase contrast overlays. (a) Using the receptor-mediated-based Qtracker kit (Invitrogen) resulted in non-uniform cellular loading with perinuclear aggregation. (b) In contrast, passively incubating hMSCs in naked QD media results in nearly 100% loading with a pattern that extends to the cell borders. (c) The field in (b) is imaged for QD fluorescence without the phase overlay to demonstrate homogeniety and brightness. The intracellular QD cluster distribution is diffusely cytoplasmic (c,d) and largely excludes the nucleus (blue, Hoechst 33342 dye). (e) QD loading efficiency was analyzed using flow cytometry. The threshold for plain hMSCs (gray line) was set such that the intensity range encompassed at least 98% of the control cells (red arrow indicates upper bound of control range). QD-positive status was designated for all cells in the QD-hMSC sample having intensities above the range set for the control group. In four experiments, QD-positive cells (black line) were found in 96% of over 17,000 viable cells. (f) When colchicine-conditioned cells are incubated with colchicine-containing QD media, the uptake is dramatically reduced. The cells in panel (f, colchicine) and (f, inset, no colchicine) can be directly compared, as the incubation periods were identical and the cells were imaged using the same microscope and camera settings. (g-i) hMSCs continually take up QDs from the incubation media. Cells incubated in QD media for (g) 1, (h) 3, and (i) 24 hours are all imaged using the same microscope and camera settings. Images are grayscale for clarity. Because of the different levels of loading, the exposure time (380 ms) used to image all three samples is clearly too high for the 24-hour-incubated cells; most of the QD clusters in the image are overexposed. Scale bar a, b=50 µm. Scale bar c=100 µm. Scale bar on d, f–i=25 µm FIG. 2. QDs retain their brightness and cytoplasmic distribution for up to 6 weeks in vitro and are not transferred to unloaded cells. QD-hMSCs were fixed onto slides and stained with Hoechst 33342 dye. The cells were imaged for QD fluorescence at (a) 2 days, (b) 16 days and (c) 44 days after loading. Only the Hoechst (blue) channels of these images have been post-processed to enhance contrast; QD channels (red) are displayed as imaged. As cells divide, they split their cytoplasmic contents to each daughter cell, diluting the ultimate concentration of QDs in progeny over time. Therefore, exposure times of excitation light need to be increased to optimally capture QD images of cells that have been through multiple divisions. Microscope and camera settings are the same for images (a) and (b), but in (c), cells are imaged for 655-nm (red) emission using triple the exposure time. The QDs in (a) are overexposed at this setting, with some dots clearly saturating the image. (d) QD-loaded and plain hMSCs proliferate similarly, as measured by a mitochondrial dehydrogenase assay (N=12). (e) Green (GFP transfected) and red (QD-loaded) hMSCs in direct apposition were imaged live to look for QD transfer to neighboring cells (colors have been enhanced for contrast). In a separate experiment, QD-hMSCs were mechanically lysed and then added to cultured canine myocytes for 24 hours. (f) A myocyte (right) sits near a live QD-hMSC that survived the lysis and attached to the coverslip. Floating QD clusters from the lysed cells are apparent in the media but were not internalized by the myocytes. Live cell images in (e) and (f) were acquired on an Olympus inverted fluorescence microscope using a GFP and a Texas Red filter, which does not optimally image the 655-nm QD signal. Scale bar a-c=25 µm. Scale bar e, f=50 µm FIG. 3. The presence of intracellular QDs does not affect ability of cells to overexpress genes after transfection. QD-hMSCs and plain hMSCs were each transfected with the HCN2-pIRES-EGFP plasmid via electroporation. Two days after transfection, both groups of cells expressed similar levels of GFP and cells expressing GFP from both groups were patch clamped to record the HCN2-induced currents. The currents provided were from a holding potential of −40 mV and included steps between −40 mV and −160 mV in −10 mV increments. Similar levels of HCN2-induced current were recorded from (a) unloaded and (b) QD-loaded hMSCs. Additionally, the electroporation process did not alter the cytoplasmic distribution of QDs (b, inset). Imaging for these experiments was carried out on the Olympus microscope using the Texas Red filter to visualize QDs in live cells; this filter set does not optimally visualize QD loading. Scale bar on b inset=50 µm FIG. 4. QD-hMSCs can be delivered to the canine heart on an ECM scaffold and identified 8 weeks later. QD-hMSCs were delivered to the canine ventricle via implantation of an ECM patch. Eight weeks later, tissue was explanted and fixed. Panel (a) shows fixed tissue from one animal with a blue line circumscribing the region analyzed (and imaged transmurally in panel c) and a black dotted ellipse approximating the patch borders. Straight dark black lines in the image are dissecting pins that were used to secure the tissue while photographing. The region outlined in blue was (a) frozen and sectioned transmurally at 10-µm and (b) imaged for QD fluorescence (655 nm) and phase contrast. (c) The plane of section is transmural from epicardium (top) to endocardium (bottom); a green circle highlights the region where QDs were found (imaged in b). Some tissue sections were stained with Hoechst 33342 to visualize nuclei. Panel (b, inset) shows QD-hMSCs amidst endogenous tissue (asterisks denote endogenous nuclei). Scale bar on a, c=20 mm. Scale bar on b=50 µm, inset=10 µm FIG. 5. QDs can be used to identify single hMSCs after injection into the rat heart and further used to reconstruct the 3-D distribution of all delivered cells. Rat hearts were injected with QD-hMSCs. Fixed, frozen sections were cut transversely (plane shown in b, inset) at 10-µm and mounted onto glass slides. Sections were imaged for QD fluorescence emission (655-nm) with phase overlay to visualize tissue borders. QD-hMSCs can be visualized at (a) low power, and (a, inset) high power (Hoechst 33342 dye used to stain nuclei blue). In (a, inset), endogenous nuclei can be seen adjacent to the delivered cells in the mid-myocardium (arrows). Serial low power images were registered with respect to one another and (b) binary masks were generated, where white pixels depict the QD-positive zones in the images. The vertical line in (b, inset) represents the z axis, which has a zero value at the apex of the heart. The binary masks for all of the QD-positive sections of the heart were compiled and used to generate the 3-D reconstruction of delivered cells in the tissue. QD-hMSCs remaining in the tissue adhesive on the epicardial surface (and not within the cardiac syncytium) were excluded from the reconstruction. (c) QD-hMSC reconstruction in an animal that was terminated 1 hour after injection. (d) Reconstruction from an animal euthanized 1 day after injection with orientation noted in inset. Our reconstructions in (c) and (d) do not account for all of the approximately 100,000 hMSCs delivered through the needle. Some of these cells undoubtedly leaked out of the needle track, while others may not have survived the injection protocol. The views of both reconstructions (c) and (d) are oriented for optimal static visualization (and also have different scales and are situated at different positions along the z-axis depending on the distance of the injection site from the apex of the heart); see Movies for complete 3-D representations from all perspectives. (e) One day after injection into the heart, the pattern of QD-hMSCs is well-organized and appears to mimic the endogenous myocardial orientation (dotted white line highlights myofibril alignment). Complete representations of the spatial localization of QD-hMSCs in the heart permits further quantitative analyses. (f) One parameter that can be computed is the distance of individual cells from the centroid of the total cell mass. The plots show the percentage of cells at a distance less than or equal to x for both the 1-hour and 1-day rats. At both time points, most of the cells are within 1.5 mm of the centroid. Scale bar on a=500 µm, inset=20 µm. Scale bar on b, inset=1 cm. Scale bar on e=500 µM FIG. 6. QDs do not interfere with differentiation capacity of hMSCs in vitro or in vivo. QD-hMSCs or unloaded hMSCs were induced to differentiate in vitro along adipogenic and osteogenic lineages. After the adipogenic induction period both (a) unloaded hMSCs and (b) QD-hMSCs displayed characteristic adipocyte morphology, with prominent lipid vacuoles. The percent of differentiated versus undifferentiated cells was similar between these two groups. (c) At high power, adipocytes from the QD-hMSC group are seen with QDs (red fluorescence) interspersed between lipid vacuoles. After the osteogenic induction period both (a) unloaded hMSCs and (b) QD-hMSCs that were initially spindle shaped adapted a more cobblestone-like morphology typical of osteocytes and tended to cluster on the dish. (f) At high power a cobblestone-shaped osteocyte from the QD-hMSC group retains the QD label (red) after the differentiation process. QD-hMSCs were delivered in vivo to the canine ventricle on an ECM patch. (g) After 8 weeks, some of these QD-positive cells (red) express the endothelial marker PECAM-1 (green), suggesting differentiation of these cells along and endothelial lineage. A high-power view of QD-positive cell with co-localized PECAM-1 expression is shown in (g, inset). Scale bars on a,b,d,e=200 µm Scale bars on c,f=50 µm Scale bar on g=20 µm, inset=5 µm FIG. 7. QDs can be visualized using µCT. QD-hMSCs were (a) loaded and imaged, and then formed into a pellet overnight. (b) The QD-hMSC pellet and a pellet formed from unloaded hMSCs were each embedded in a separate siloxane mold. Both phantom molds were scanned using µCT and images were reconstructed. In (c) a 2-D image of one section through the QD-hMSC pellet is shown. (d) Average densities for pellets formed from QD-loaded (N=16) and unloaded (N=12) hMSCs were calculated and normalized to the average density of the unloaded pellet. QD-hMSCs were roughly 27% denser than unloaded hMSCs. (e) The 3-D reconstruction of the scanned region of QD-hMSC pellet is shown. Scale bar on a=200 µm. Scale bar on b=1 cm. Scale bar on c=1 mm.

5. DETAILED DESCRIPTION OF THE INVENTION

The present invention provides methods and compositions relating to the labeling of target cells with nanometer scale fluorescent semiconductors referred to as quantum dots (QDs). The methods and compositions of the invention provide a means for assessing the safety and efficacy of therapies based on the administration of cells, for example stem cells, into a subject in need of treatment.

5.1. Quantum Dot (OD) Labeling of Cells

The present invention provides a method for transfer of QDs into the cytosol of a cell comprising contacting target cells with negatively charged QDs. The method of the invention results in delivery of a tracking fluorescent signal into the cytosol of said target cell via a passive endocytosis delivery process. The delivery system of the present invention can be used with virtually any type of biological cell population, including, mammalian cells. The specific cell type used will typically vary depending upon the type of cell tracking that is sought to be monitored. For example, mammalian cells and specifically, human cells or animal cells containing QDs are typically preferred for determining the safety and efficacy of potential human therapies. Additionally, endothelial progenitor cells may be labeled with QDs to track, for example, early migration and incorporation of endothelial stem cells into blood vessels. QD-labeled hematopoeitic stem cells may be used to track development of said labeled cells into the different functional cell types of the blood. While it is understood that the delivery system of the present invention may be used to deliver QDs into a variety of different cell types, for simplicity, the invention is described in detail below for use with stem cells. However, the methods of the invention may be applied equally as well for use with other cell types.

In an embodiment of the invention, the target cells to which QDs are to be delivered are mammalian cells, including but not limited to, mammalian stem cells. In a preferred embodiment of the invention, the stem cells are mesenchymal stem cells (MSCs). In another embodiment of the invention, the stem cells are human stem cells, or human MSCs (hMSCs).

As used herein, "stem cell" refers to any cell having the potential to differentiate into one or more different cell types. Such cells include, but are not limited to, stem cells derived from a variety of different sources including, for example, bone marrow, embryonic blastocysts or yolk sac, spleen, blood, including peripheral blood and umbilical cord blood, adipose tissue and other tissues and organs. Such stem cells include, but are not limited to, hematopoietic stem cells, endothelial progenitor cells or embryonic stem cells. In a preferred embodiment of the invention, mammalian MSCs are utilized in the practice of the invention. In a preferred embodiment of the invention the utilized MSCs are derived from a human.

Stem cells may be obtained from a variety of different donor sources. In a preferred embodiment, autologous stem cells are obtained from the subject who is to receive the transplanted stem cells to avoid immunological rejection of foreign tissue. In yet another preferred embodiment of the invention, allogenic stem cells may be obtained from donors who are genetically related to the recipient and share the same transplantation antigens on the surface of their stem cells. Alternatively, stem cells may be derived from antigenically matched (identified through a national registry) donors. In instances where antigenically matched stem cells cannot be located, non-matched cells may be used, however, it may be necessary to administer immunosuppressive agents to prevent recipient rejection of the donor stem cells.

Procedures for harvest and isolation of such stem cells are well known to those of skill in the art and do not differ from those used in conventional stem cell transplantation. Adult stem cells may be derived from bone marrow, peripheral blood, adipose tissue and other adult tissues and organs. For derivation of embryonic stem cells, stem cells can be extracted from the embryonic inner cell mass during the blastocyst stage. Fetal stem cells may be derived from the liver, spleen, brain or heart of fetuses, 4-12 weeks gestation, following elective abortions, terminated ectopic pregnancies or spontaneous miscarriages.

In a non-limiting embodiment of the invention, antibodies that bind to cell surface markers selectively expressed on the surface of stem cells may be used to identify or enrich for populations of stem cells using a variety of methods. Such markers include, for example, CD34, SSEA3, SSEA4, anti-TRA1-60, anti-TRA1-81 or c-kit.

In an embodiment of the invention, MSCs may be derived from bone marrow aspirates. For example, 10 ml of marrow aspirate is collected into a syringe containing 6000 units of heparin to prevent clotting, washed twice in phosphate buffer solution (PBS), added to 20 ml of control medium (DMEM containing 10% FBS), and then centrifuged to pellet the cells and remove the fat. The cell pellet is then resuspended in control medium and fractionated at 1100 g for 30 min on a density gradient generated by centrifugation of a 70% percoll solution at 13000 g for 20 minutes. The mesenchymal stem cell-enriched, low density fraction is collected, rinsed with control medium and plated at a density of $10^7$ nucleated cells per 60 mm$^2$ dish. Alternatively, MSCs (Poietics™ hMSCs) to be used in the practice of the invention can be purchased from Clonetics/Bio Whittaker (Walkersville, M.D.).

In a specific embodiment of the invention, MSCs are grown on polystyrene tissue culture dishes and maintained at 37° C. in humidified 5% $CO_2$ in Mesenchymal Stem Cell Growth Media supplemented with L-glutamine, penicillin and serum (MSCGM BulletKit, Cambrex). Cells are re-plated for passaging once every two weeks. The MSCs are then cultured in control medium at 37° C. in a humidified atmosphere containing 5% $CO_2$.

In yet another embodiment of the invention, late passage MSCs, which are substantially unable to differentiate, may be labeled with QDs using the delivery system of the present invention. As used herein, "late passage MSCs" are those cells that have been passaged at least nine times. Additionally, the QD-labeled MSCs of the invention express CD29, CD44, CD54 and HLA class I surface markers while failing to express CD14, CD45, CD34 and HLA class II surface markers.

In an embodiment of the invention, the cells to be labeled with QDs may be genetically engineered to express one or more genes encoding physiologically active proteins of interest. Such proteins include, for example, those proteins capable of providing biological pacemaker activity. Such engineered cells are described in detailed below. The cells may be genetically engineered using techniques well known in the art to express proteins that further enhance the ability of such cells to provide biological pacemaker activity. Such techniques include, for example, in vitro recombinant DNA techniques, synthetic techniques, and in vivo genetic recombination. (See, for example, the techniques described in Sambrook J et al. 2000. Molecular Cloning: A Laboratory Manual (Third Edition), and Ausubel et al (1996) Current Protocols in Molecular Biology John Wiley and Sons Inc., USA). Any of the methods available in the art for gene delivery into a host cell can be used according to the present invention to deliver genes into the target cell population. Such methods include electroporation, lipofection, calcium phosphate mediated transfection, or viral infection. For general reviews of the methods of gene delivery see Strauss, M. and Barranger, J. A., 1997, Concepts in Gene Therapy, by Walter de Gruyter & Co., Berlin; Goldspiel et al., 1993, Clinical Pharmacy 12:488-505; Wu and Wu, 1991, Biotherapy 3:87-95; Tolstoshev, 1993, Ann. Rev. Pharmacol. Toxicol. 33:573-596; Mulligan, 1993, Science 260:926-932; and Morgan and Anderson, 1993, Ann. Rev. Biochem. 62:191-217; 1993, TIBTECH 11(5):155-215.

In an embodiment of the invention, the target cells to be labeled with QDs may further comprise an exogenous molecule including, but are not limited to, oligonucleotides, polypeptides, or small molecules, and wherein said QD-labeled cell is capable of delivering said exogenous molecule to an adjacent cell, or cells at a greater distance, via the gap junctions of the adjacent cells. Delivery of the exogenous molecule to adjacent cells, or cells at a greater distance, via the gap junctions of the adjacent cells may be used to provide biological pacemaker activity.

QDs to be used in the practice of the invention may be composed of various semiconductor materials such as, for example, CdS, CdSe, CdTe, CdTe/ZnS or CdSe/ZnS. In a preferred embodiment of the invention, the QDs for use in the practice of the invention are those having a net negative charge. Such negatively charged QDs may be formed through conjugation of negatively charged groups onto the surface of the QD. In a specific embodiment of the invention, the negative charge of the QDs comes from carboxyl groups on the surface of a polymer surface.

Further, for use in the present invention QDs are preferably those that emit light at wavelengths of between 525-800. In a preferred embodiment of the invention, the QD is one that emits light at a wavelength of 655.

In an embodiment of the invention, various biological or chemical moieties may be conjugated to the surface of QDs as a means for delivery of said moiety into the cytosol of the target cell. For example, streptavidin, which binds to biotin with extremely high affinity, may be conjugated to negatively charged QDs. Through conjugation of strepavidin to QDs, a system is provided whereby streptavidin-conjugated QDs can be coupled to biotin-conjugated magnetic nanoparticles (superparamagnetic iron oxide, SPIO) through the strepavidin/biotin high-affinity reaction. Loading of MSCs using such hybrid QD-SPIO particles permits detection of said cells in vitro via the emitted QD fluorescence or by staining the cells with Prussian Blue to detect iron oxide. Additionally, such loaded cells can be delivered to animals and tracked non-invasively in vivo using MRI.

The delivery system of the present invention comprises contacting a target cell population with negatively charged QDs for a time sufficient to permit transfer of the QDs into the cytosol of the target cell. In an embodiment of the invention, the target cells are cultured, using routine tissue culture methods well known to those of skill in the art, to less than 100% confluence, preferable between 80-85% confluence. Cells are then washed with a buffer, such as a phosphate-buffered saline (PBS) and a solution of QDs is added to the target cells. In an embodiment of the invention, the QD solution comprises a mixture of the tissue culture media in which the cells are cultured and QDs.

In a preferred embodiment of the invention the media comprises fetal calf serum. The solution of QDs contains QDs at a concentration of 8-8.5 nM. Cells are incubated with the QDs for a time sufficient to permit efficient transfer of the QDs into the cytosol of the target cells. Transfer of QDs into the target cells can be monitored using, for example, fluorescent microscopy or flow cytometry. In an embodiment of the invention, the QDs are incubated for about 6-48 hours.

In a specific embodiment of the invention, MSCs cells are grown to approximately 85% confluence on polystyrene tissue culture dishes. An 8.2 nM solution of 655 ITK Carboxyl QDs is prepared in complete MSCGM and vortexed for 60 seconds. Cells are washed once in phosphate-buffered saline (PBS) and incubated in the QD solution for up to 24 hours at 37° C.

The present invention provides labeled target cells that have taken up QDs through use of the delivery system of the invention. The QD labeled cells of the invention lack perinuclear aggregation and show a uniform diffuse cytoplasmic labeling. In a preferred embodiment of the invention the labeled cells are stem cells, preferably MSCs. Also within the scope of the invention are QD labeled cells that have been genetically engineered to express a desired protein of interest. For example, QD labeled cells may be engineered to express HCN proteins, mutants and chimeras capable of providing biological pacemaker function.

The present invention further relates to pharmaceutical compositions comprising cells labeled with QDs and a pharmaceutically acceptable carrier. Pharmaceutically acceptable carriers are well known to those skilled in the art and include, but are not limited to, 0.01-0.1M and preferably 0.05M phosphate buffer, phosphate-buffered saline (PBS), or 0.9% saline. Such carriers also include aqueous or non-aqueous solutions, suspensions, and emulsions. Aqueous carriers include water, alcoholic/aqueous solutions, emulsions or suspensions, saline and buffered media. Examples of non-aqueous solvents are propylene glycol, polyethylene glycol, vegetable oils such as olive oil, and injectable organic esters such as ethyl oleate. Preservatives and other additives, such as, for example, antimicrobials, antioxidants and chelating agents may also be included with all the above carriers.

Another aspect of the present invention relates to kits for labeling target cells with QDs utilizing the methods of the present invention. Kits of the present invention comprise negatively charged quantum dots. Kits of the present invention may further comprise additional reagents, buffers and/or apparatus for use in labeling target cells with QDs via the method of the present invention as well as instructions for use of the kit to label cells.

5.2 Use of QD-Labeled Mesenchymal Cells for Generation of Biological Pacemaker Activity With the advent of clinical trials for tissue repair employing stem cells, it is essential for both safety and efficacy to know the spatial distribution of cells delivered in vivo in animal models and in humans. Accordingly, the present invention encompasses methods for determining the fate and distribution of administered stem cells in a mammal comprising administering QD labeled stem cells to a subject followed by an assessment of the spatial distribution of stem cells. Moreover, following administration of the labeled cells, the safety and efficacy of such stem cell administration may be determined.

In one embodiment, the present invention relates to the generation of biological pacemaker activity based on the expression of wild type, mutant or chimeric HCN ion channels in QD-labeled MSCs for treatment of cardiac disorders. Methods for generating biological pacemaker activity are disclosed in U.S. Pat. No. 6,849,611 and, U.S. patent application Ser. Nos. 10/342,506 and 10/757,827 each of which are incorporated by reference herein in their entirety.

As used herein, "biological pacemaker activity" shall mean the rhythmic generation of an action potential originating from the introduction of biological material in a cell or a syncytial structure comprising the cell. A "syncytial structure" shall mean a structure with gap junction-mediated communication between its cells.

The present invention relates to the generation of biological pacemakers with desirable clinical characteristics based on QD-labeled MSC expression of wild-type, mutant and chimeric HCN genes, and the use of these biological pacemakers to create an effective treatment for cardiac conditions. Accordingly, the present invention provides QD-labeled hMCSs comprising in vitro-recombined gene constructs encoding HCN ion channels. An "HCN ion channel" shall mean a hyperpolarization-activated, cyclic nucleotide-gated ion channel responsible for the hyperpolarization-activated cation currents that are directly regulated by cAMP and contribute to pacemaker activity in heart and brain. "mHCN" designates murine or mouse HCN; "hHCN" designates human HCN.

There are four HCN isoforms: HCN1, HCN2, HCN3 and HCN4. All four isoforms are expressed in brain; HCN1, HCN2 and HCN4 are also prominently expressed in heart, with HCN4 and HCN1 predominating in sinoatrial node and HCN2 in the ventricular specialized conducting system.

In an embodiment of the invention, the HCN channel to be expressed is HCN1, HCN2, HCN3, HCN4, or a mutant thereof. Voltage sensing and activation of HCN channels can be altered by mutation. For example, Chen et al. (2001, Proc. Natl. Acad. Sci. USA 98:11277-11282) identified three residues, E324, Y331, and R339, in the mHCN2 S4-S5 linker that, when mutated, disrupts normal channel closing. Mutation of a basic residue in the S4 domain (R318Q) prevents channel opening. Conversely, channels with R318Q and Y331S double mutations are constitutively open. Several point mutations, including R318Q, W323A, E324A, E324D, E324K, E324Q, F327A, T330A and Y331A, Y331D, Y331F, Y331K, D332A, M338A, R339A, R339C, R339D, R339E and R339Q, were also made by Chen et al. (2001, Proc. Natl. Acad. Sci. USA 98:11277-11282) to investigate in greater detail the role of the E324, Y331 and R339 residues in voltage sensing and activation. Many additional mutations in different HCN isoforms have been reported. For example, Chen et al. (2001, J Gen Physiol 117:491-504) have reported the R538E and R591E mutations in mHCNI; Tsang et al. (2004, J Biol Chem 279:43752-43759) have reported G231A and M232A in mHCNI; Vemana et al (2004, J Gen Physiol 123: 21-32) have reported R247C, T249C, K250C, I251C, L252C, S253C, L254C, L258C, R259C, L260C, S261C, C318S, S338C in mHCN2; Macri and Accili (2004, J Biol Chem 279:16832-16846) have reported S306Q, Y331D AND G404S in mHCN2; and Decher et al. (2004, J Biol Chem 279:13859-13865) have reported Y331A, Y331D, Y331S, R331FD, R339E, R339Q, I439A, S441A, S441T, D443A, D443C, D443E, D443K, D443N, D443R, R447A, R447D, R447E, R447Y, Y449A, Y449D, Y449F, Y449G, Y449W, Y453A, Y453D, Y453F, Y453L, Y453W, P466Q, P466V, Y476A, Y477A and Y481A in mHCN2. The contents of all of the above publications are incorporated herein by reference. Certain of the reported mutations listed above may confer, singly or in combination, beneficial characteristics on the HCN channel with regard to creating a biological pacemaker. The invention disclosed herein encompasses QD-labeled MSC expression of mutations in HCN channels, singly or in combinations, which enhance pacemaker activity of the channel. In a preferred embodiment, the HCN channel or mutant thereof is HCN2.

In a specific embodiment of the present invention, the mutant HCN2 channel is E324A-HCN2, Y331A-HCN2, R339A-HCN2, or Y331A,E324A-HCN2. In a preferred embodiment, the mutant HCN2 channel is E324A-HCN2.

One approach to enhancing biological pacemaker activity of a HCN channel by increasing the magnitude of the current expressed and/or speeding its kinetics of activation is to co-expressed with HCN2 its alpha subunit and beta subunit, MiRP1. MiRP1 mutations have also been reported (see e.g., Mitcheson et al., (2000, J Gen Physiol 115:229-40); Lu et al., (2003, J Physiol 551:253-62); Piper et al., (2005, J Biol Chem 280:7206-17)), and certain of these mutations, or combinations thereof, may be beneficial in increasing the magnitude and kinetics of activation of the current expressed by a HCN channel used to create a biological pacemaker. The invention disclosed herein encompasses expression in labeled MSCs all such mutations, or combinations thereof, in MiRP1.

The present invention further relates to the use of QD-labeled MSCs expressing chimeras between HCN isoforms for generating pacemaker currents in treating heart disorders. Such chimeric HCN channels may be formed by in vitro recombination of nucleotide sequences encoding portions of all four HCN isoforms to produce HCN chimeras. Chimeras of pacemaker ion channels that may be used in the practice of the invention include, but are not limited to, those chimera channels disclosed in U.S. Provisional Patent Application 60/715,934 which is incorporated by reference herein in its entirety.

A "HCN chimera" shall mean an ion channel comprised of portions of more than one type of HCN channel. For example, a chimera of HCN1 and HCN2 or HCN3 or HCN4, and so forth. In an embodiment of the invention, the portions are derived from human HCN isoforms. In addition a chimera ion channel may also comprise portions of an HCN channel derived from different species. For example, one portion of the channel may be derived from a human and another portion may be derived from a non-human.

Such chimeric HCN polypeptides provide an improved characteristic, as compared to a wild-type HCN channel, selected from the group consisting of faster kinetics, more positive activation, increased expression, increased stability, enhanced cAMP responsiveness, and enhanced neurohumoral response.

In general terms, HCN polypeptides can be divided into three major domains: (1) an amino terminal portion; (2) an intramembranous portion and its linking regions; and (3) a carboxy-terminal portion. Structure-function studies have shown that the intramembranous portions with its linking regions play an important role in determining the kinetics of gating. The C-terminal portion contains a binding site for cAMP and so is in large part responsible for the ability of the channel to respond to the sympathetic and parasympathetic nervous systems that respectively raise and lower cellular cAMP levels.

The term "HCNXYZ" (wherein X, Y and Z are any one of the integers 1, 2, 3 or 4, with the proviso that at least one of x, y and Z is a different number from at least one of the remaining) shall mean an HCN chimera channel polypeptide comprising three contiguous portions in the order XYZ wherein X is an N-terminal portion, Y is an intramembrane portion, and Z is a C-terminal portion, and wherein the number of X, Y and Z designates the HCN channel from which that portion is derived. For example, HCN112 is an HCN chimera with a N-terminal portion and intramembrane portion from HCN1 and a C-terminal portion from HCN2.

The present invention provides QD-labeled hMCSs comprising in vitro-recombined gene constructs encoding chimeric HCN channels that have fast kinetics and good responsiveness to cAMP. In one embodiment of the invention described herein, the HCN chimera comprises an amino terminal portion contiguous with an intramembranous portion contiguous with a carboxy terminal portion, wherein each portion is a portion of an HCN channel or a portion of a mutant thereof, and wherein one portion derives from an HCN channel or a mutant thereof which is different from the HCN channel or mutant thereof from which at least one of the other two portions derive.

In a specific embodiment, the mutant HCN channel from which the portion of the HCN chimera derives is E324A-HCN2, Y331A-HCN2, R339A-HCN2, or Y331A,E324A-HCN2. In a still further embodiment, the HCN chimera is a polypeptide comprising mHCN112, mHCN212, mHCN312, mHCN412, mHCN114, mHCN214, mHCN314, mHCN414, hHCN112, hHCN212, hHCN312, hHCN412, hHCN114, hHCN214, hHCN314, or hHCN414. In a specific embodiment of the invention the chimeric HCN polypeptide is hHCN212 or polypeptide mHCN212.

Other preferred embodiments include: a chimeric HCN polypeptide wherein the intramembranous portion is derived from an HCN1 channel; a chimeric HCN polypeptide wherein the intramembranous portion is D140-L400 of hHCN1; or a chimeric HCN polypeptide wherein the intramembranous portion is D129-L389 of mHCN1.

In yet another embodiment of the invention, the chimeric HCN polypeptide is a mutant HCN channel containing a mutation in a region of the channel selected from the group consisting of the S4 voltage sensor, the S4-S5 linker, S5, S6 and S5-S6 linker, the C-linker, and the CNBD.

In yet another embodiment of the invention, the chimeric HCN polypeptide is a mutant, wherein the mutant portion is derived from mHCN2 having the sequence set forth in SEQ ID NO:C and comprises E324A-mHCN2, Y331A-mHCN2, R339A-mHCN2, or Y331A,E324A-mHCN2. In a specific embodiment of the invention, the mutant portion comprises E324A-mHCN2.

In addition to recombinant expression of wild-type, mutant and chimeric HCN ion channels, the QD-labeled MSCs may further expresses at least one cardiac connexin, including for example, Cx43, Cx40, or Cx45.

To practice the methods of the invention it will be necessary to recombinantly express wild-type, mutant and chimeric HCN ion channels. The cDNA sequence and deduced amino acid sequence of HCN ion channels have been characterized. Sequences of the HCN ion channels are available from public databases.

HCN ion channel nucleotide sequences may be isolated using a variety of different methods known to those skilled in the art. For example, a cDNA library constructed using RNA from a tissue known to express the HCN ion channels can be screened using a labeled HCN channel probe. Alternatively, a genomic library may be screened to derive nucleic acid molecules encoding the HCN ion channel protein. Further, such nucleic acid sequences may be derived by performing a polymerase chain reaction (PCR) using two oligonucleotide primers designed on the basis of known HCN ion channel nucleotide sequences. The template for the reaction may be cDNA obtained by reverse transcription of mRNA prepared from cell lines or tissue known to express the HCN ion channel of interest.

HCN ion channels, polypeptides and peptide fragments, mutated, truncated, deleted and chimeric forms of the HCN channels can be prepared for a variety of uses, including but not limited to, the production of biological pacemaker activity. Such proteins may be advantageously produced by recombinant DNA technology using techniques well known in the art for expressing a nucleic acid. Such methods can be used to construct expression vectors containing the HCN ion channel nucleotide sequences and appropriate transcriptional and translational control signals. These methods include, for example, in vitro recombinant DNA techniques, synthetic techniques, and in vivo genetic recombination. (See, for example, the techniques described in Sambrook J et al. 2000. Molecular Cloning: A Laboratory Manual (Third Edition), and Ausubel et al (1996) Current Protocols in Molecular Biology John Wiley and Sons Inc., USA).

A variety of host-expression vector systems may be utilized to express the HCN ion channel nucleotide sequences in QD-labeled MSCs. For long-term, high yield production of recombinant HCN ion channel expression, such as that desired for development of biological pacemakers, stable expression is preferred. Rather than using expression vectors which contain origins of replication, host cells can be transformed with DNA controlled by appropriate expression control elements and a selectable marker gene, i.e., tk, hgprt, dhfr, neo, and hygro gene, to name a few. Following the introduction of the foreign DNA, engineered MSCs may be allowed to grow for 1-2 days in enriched media, and then switched to a selective media. Any of the methods for gene delivery into a host cell available in the art can be used according to the present invention. In different embodiments of the invention, the gene delivery method may be performed either before or after QD loading of the MSCs. Such methods include, for example, electroporation, lipofection, calcium phosphate mediated transfection, or viral infection. For general reviews of the methods of gene delivery see Strauss, M. and Barranger, J. A., 1997, Concepts in Gene Therapy, by Walter de Gruyter & Co., Berlin; Goldspiel et al., 1993, Clinical Pharmacy 12:488-505; Wu and Wu, 1991, Biotherapy 3:87-95; Tolstoshev, 1993, Ann. Rev. Pharmacol. Toxicol. 33:573-596; Mulligan, 1993, Science 260:926-932; and Morgan and Anderson, 1993, Ann. Rev. Biochem. 62:191-217; 1993, TIBTECH 11(5):155-215. Exemplary methods are described below.

The present invention further provides compositions comprising QD-labeled MSCs expressing wild-type, mutant or chimera HCN channels, as described above. The compositions of the invention may further comprise pharmaceutically acceptable carrier.

The present invention relates to a method for tracking the distribution and/or fate of QD-labeled cells that have been administered to a subject afflicted with a cardiac rhythm disorder comprising (i) administering QD-labeled MSCs, expressing wild-type, mutant or chimeric HCN polypeptides, to a region of the subject's heart, wherein expression of the HCN polypeptide in said region of the heart is effective to induce a pacemaker current in the heart and (ii) detecting the distribution and/or fate of QD-labeled cells that have been administered to said subject. In a specific embodiment of the invention, the QD-labeled MSC forms a functional syncytium with the heart.

In an embodiment of the invention, the QD-labeled MSC, expressing wild-type, mutant or chimeric HCN polypeptides is administered to the region of the heart by injection, catheterization, surgical insertion, or surgical attachment. The QD-labeled MSCs may be locally administered by injection or catheterization directly onto or into the heart tissue. The QD-labeled MSCs may be administered by injection or catheterization into at least one of a coronary blood vessel or other blood vessel proximate to the heart. The QD-labeled MSCs may be administered to a region of an atrium or ventricle of the heart.

Cardiac rhythm disorders that may be treated using the methods and compositions of the invention include, but are not limited to, sinus node dysfunction, sinus bradycardia, marginal pacemaker function, sick sinus syndrome, tachyarrythmia, sinus node reentry tachycardia, atrial tachycardia from an ectopic focus, atrial flutter, atrial fibrillation, bradyarrythmia, or cardiac failure, wherein the QD-labeled MSCs expressing wild-type, mutant or chimeric HCN polypeptides, are administered to the right or left atrial muscle, sinoatrial node, or atrioventricular junctional region of the subject's heart.

Disorders to be treated also include a conduction block, complete atrioventricular block, incomplete atrioventricular block, or bundle branch block, wherein the QD-labeled MSC, expressing wild-type, mutant or chimeric HCN polypeptides, are administered to a region of the subject's heart so as to compensate for the impaired conduction in the heart. Such regions include the ventricular septum or free wall, atrioventricular junction, or bundle branch of the ventricle.

The present invention additionally provides a method of inhibiting the onset of a cardiac rhythm disorder in a subject prone to such disorder comprising administering QD-labeled MSCs, expressing wild-type, mutant or chimeric HCN polypeptides, to a region of the subject's heart, wherein expression of the HCN polypeptide in the heart is effective to induce a pacemaker current in the heart and thereby inhibit the onset of the disorder in the subject.

5.3. Use of QD-Labeled Human Mesenchymal Stem Cells for Generation of a Bypass Bridge The present invention also provides methods and compositions for assessing the spatial distribution of QD-labeled MSCs utilized for treating a subject afflicted with a cardiac rhythm disorder wherein a bypass bridge is provided in the heart that will take over the function of a diseased atrioventricular or sinus node. Methods for production of such bypass bridges are disclosed in International Patent Application No. PCT/US04/042953 which is incorporated by reference herein in its entirety.

In an embodiment of the invention, the bypass bridge may be made from a monolayer of QD-labeled MSCs or QD-labeled MSCs on an extracellular matrix patch without incorporation of additional molecular determinants of conduction. Here the cells' own ability to generate gap junctions that communicate electrical signals is used as a means to propagate an electronic wave from cell to cell.

Accordingly, the present invention provides a bypass bridge comprising a tract of gap junction-coupled QD-labeled hMSCs having a first end and a second end, both ends capable of being attached to two selected sites in a heart so as to allow the conduction of an electrical signal across the tract between the two sites, wherein the cells functionally express a sodium channel. Such sodium channels include, for example, a SKM-1 channel which may further comprise an alpha subunit and/or an accessory subunit.

In a specific embodiment of the invention, the first end of the tract is capable of being attached to the atrium and the second end of the tract is capable of being attached to the ventricle, so as to allow conduction of an electrical signal across the tract from the atrium to the ventricle.

In an embodiment of the invention, the QD-labeled MSCs of the bypass bridge may further functionally express a pacemaker ion channel which induces a pacemaker current so as to induce a pacemaker current in said cells. The pacemaker ion channel is at least one of (a) a hyperpolarization-activated, cyclic nucleotide-gated (HCN) ion channel, mutant or chimera thereof, (b) an HCN channel subunit, i.e., alpha subunit; and (c) a MiRP1 beta subunit. Mutants and chimeras HCN channels are described in detail above. In an embodiment of the invention, the pacemaker ion channel is expressed in cells in the first end of the tract. In a specific embodiment, the cells expressing the pacemaker ion channel are located in a region extending 0.5 mm from the first end.

The QD-labeled MSCs in the tract may further functionally express one or more additional channels, including but not limited to, a potassium channel which may further comprise a Kir2.1 or Kir2.2 alpha subunit and/or an accessory subunit; and an L-type calcium channel which may further comprise an alpha subunit and an accessory subunit.

Thus, the QD-labeled MSCs of the bypass bridge may further functionally express one or more of at least one cardiac connexin, an alpha subunit with accessory subunits of an L-type calcium channel, an alpha subunit with or without accessory subunits of a potassium channel, or a second sodium channel, so as to change the voltage-time course of repolarization and/or refractoriness of the heart. Connexins that may be expressed include, but are not limited to, Cx43, Cx40, or Cx45.

The present invention provides a method of making a bypass bridge for implantation in a heart, which is composed of QD-labeled MSCs comprising: (a) transfecting a MSC with, and functionally expressing therein, a nucleic acid encoding a sodium channel; and (b) growing the transfected MSC into a tract of cells having a first and a second end capable of being attached to two selected sites in the heart, wherein the cells are physically interconnected via electrically conductive gap junctions. Moreover, the MSCs to be used for making the bypass bridge are loaded with QDs using the methods of the present invention either before or after transfection.

In an embodiment of the invention, cells in the tract are transfected with a nucleic acid encoding a pacemaker ion channel, wherein the nucleic acid is functionally expressed so as to induce a pacemaker current in the cells. The pacemaker ion channel is at least one of (a) a hyperpolarization-activated, cyclic nucleotide-gated (HCN) ion channel or a mutant or chimera thereof, (b) an HCN channel subunit, i.e., alpha subunit; and (c) a MiRP1 beta subunit.

The MSCs may be further transfected with, at least one nucleic acid encoding one or more of at least one connexin, an alpha subunit with accessory subunits of an L-type calcium channel, an alpha subunit with or without accessory subunits of the potassium channel, or a second sodium channel, such that implantation of a bypass bridge in a heart changes the voltage-time course of repolarization and/or refractoriness of the heart.

The present invention provides a method of assessing the fate and distribution of QD-labeled MSCs implanted as a bypass bridge in a heart comprising: (a) making a bypass bridge utilizing QD-labeled cells; (b) selecting a first and a second site in the heart; (c) attaching the first end of the tract to the first site and the second end of the tract to the second site; so as to thereby implant a bypass bridge in the heart that allows the conduction of an electrical signal across the tract between the two sites, and (d) assessing the fate and distribution of the QD-labeled cells. In an embodiment of the invention, the electrical signal is generated in the atrium by the sinus node or an electronic pacemaker.

The present invention further provides a method of assessing the fate and distribution of QD-labeled MSCs for use in treating a disorder associated with an impaired conduction in a subject's heart comprising: (a) transfecting a MSC with a nucleic acid encoding a sodium channel, wherein the cell functionally expresses the sodium channel (b) loading the MSCs with QDs either before or after transfection; (c) growing the transfected MSC into a tract of cells having a first end and a second end, wherein the cells are physically interconnected via electrically conductive gap junctions; (d) selecting a first site and a second site in the heart between which sites conduction is impaired; (e) attaching the first end of the tract to the first site and the second end of the tract to the second site; so as to allow the conduction of an electrical signal across the tract between the two sites and thereby treat the subject and (f) detecting the fate and distribution of QD-labeled MSCs.

The present invention relates to a method of assessing the fate and/or distribution of QD labeled MSCs for treating a disorder associated with an impaired conduction and impaired sinus node activity in a subject's heart comprising: (a) transfecting a QD-labeled MSC with at least one nucleic acid encoding a sodium channel and a pacemaker ion channel, wherein the QD-labeled MSC functionally expresses the sodium channel and the pacemaker ion channel; (b) loading MSCs with QDs either before or after transfection; (c) growing the transfected QD-labeled MSC into a tract of cells having a first end and a second end, wherein the cells are physically interconnected via electrically conductive gap junctions; (d) selecting a first site in the left atrium of the heart and a second site, between which sites conduction is impaired; and (e) attaching the first end of the tract to the first site and the second end of the tract to the second site; so as to allow the propagation of an electrical signal generated by the sinus node and/or tract of cells between the two sites and thereby treat the subject.

The preparation of a bypass bridge in this fashion not only will facilitate propagation from atrium to ventricle, but will provide sufficient delay from atrial to ventricular contraction to maximize ventricular filling and emptying. The goal is to mimic the normal activation and contractile sequence of the heart. Moreover, this approach, when used with biological pacemaker technology to improve atrial impulse initiation in the setting of sinus node disease offers a completely physiologic system. Thus, the present methods comprise the use in a subject's heart of various combinations of a biological pacemaker and/or biological atrioventricular bridge or atrioventricular node composed of QD-labeled cells.

5.4. Use of Biological Pacemakers and Bridges in Tandem with Electronic Pacemakers The present invention relates to the use of biological pacemakers and/or bypass bridges composed of QD labeled MSCs either alone or in combination with electronic pacemakers. Detailed descriptions of the individual components of a tandem pacemaker have been previously published. For example, details of electronic pacemakers per se may be found in U.S. Pat. Nos. 5,983,138; 5,318,597; 5,376,106; Pacemaker Timing Cycles and Electrocardiography, David L. Hayes, M.D., Chapter 6 of Cardiac Pacing and Defibrillation, pp. 201-223, Mayo Foundation, 2000; and Types of Pacemakers and Hemodynamics of Pacing, Chapter 5 of A Practical Guide to Cardiac Pacing-Fifth Edition, pp. 78-84, Cippincott Williams & Wilkins, Philadelphia (2000) all of which are incorporated herein by reference. Additionally, tandem cardiac pacemakers to be used in combination with biological pacemakers and/or bypass bridges are described in U.S. Patent Application Ser. Nos. 60/701,312 and 60/781,723 each of which are incorporated by reference herein in their entirety.

In preferred embodiments of the subject invention, the electronic pacemaker is programmed to produce its pacemaker signal on an "as-needed" basis, i.e., to sense the biologically generated beats and to discharge electrically when there has been failure of the biological pacemaker to fire and/or atrioventricular bridge to conduct current for more than a preset time interval. At this point the electronic pacemaker will take over the pacemaker function until the biological pacemaker resumes activity. Accordingly, a determination should be made on when the electronic pacemaker will produce its pacemaker signal. State of the art pacemakers have the ability to detect when the heart rate falls below a threshold level in response to which an electronic pacemaker signal should be produced. The threshold level may be a fixed number, but preferably it varies depending on patient activity such as physical activity or emotional status. When the patient is at rest or pursuing light activity the patient's baseline heart rate may be at 60-80 beats per minute (bpm) (individualized for each patient), for example. Of course, this baseline heart rate varies depending on the age and physical condition of the patient, with athletic patients typically having lower baseline heart rates. The electronic pacemaker can be programmed to produce a pacemaker signal when the patient's actual heart rate (including that induced by any biological pacemaker) falls below a certain threshold baseline heart rate, a certain differential, or other ways known to those skilled in the art. When the patient is at rest the baseline heart rate will be the resting heart rate. The baseline heart rate will likely change depending on the physical activity level or emotional state of the patient. For example, if the baseline heart rate is 80 bpm, the electronic pacemaker may be set to produce a pacemaker signal when the actual heart rate is detected to be about 64 bpm (i.e., 80% of 80 bpm).

The electronic component can also be programmed to intervene at times of exercise if the biological component fails, by intervening at a higher heart rate and then gradually slowing to a baseline rate. For example, if the heart rate increases to 120 bpm due to physical activity or emotional state, the threshold may increase to 96 bpm (80% of 120 bpm). The biological portion of this therapy brings into play the autonomic responsiveness and range of heart rates that characterize biological pacemakers and the baseline rates that function as a safety-net, characterizing the electronic pacemaker. The electronic pacemaker may be arranged to output pacemaker signals whenever there is a pause of an interval of X % (e.g., 20%) greater than the previous interval, as long as the previous interval was not due to an electronic pacemaker signal and was of a rate greater than some minimum rate (e.g., 50 bpm).

In an embodiment of the present methods, the electronic pacemaker senses the heart beating rate and produces a pacemaker signal when the heart beating rate falls below a specified level. In a further embodiment, the specified level is a specified proportion of the beating rate experienced by the heart in a reference time interval. In a still further embodiment, the reference time interval is an immediately preceding time period of specified duration.

The present invention provides a tandem pacemaker system comprising (1) an electronic pacemaker, and (2) a biological pacemaker, wherein the biological pacemaker comprises implantable QD-labeled MSC that functionally expresses a wild type, mutant or chimeric hyperpolarization-activated, cyclic nucleotide-gated (HCN) ion channel, and wherein the expressed HCN channel generates an effective pacemaker current when the cell is implanted into a subjects heart. Wild type, mutant and chimeric HCN channel expression can be achieved using the methods described above.

In an embodiment of the invention, the biological pacemaker of the tandem system comprises at least about 200,000

QD-labeled MSCs. In another embodiment of the invention, the biological pacemaker comprises at least about 700,000 QD-labeled MSCs.

In a specific embodiment of the invention, a tandem pacemaker system is provided comprising (1) an electronic pacemaker, and (2) a biological pacemaker, wherein the biological pacemaker comprises an implantable QD-labeled MSC, wherein said cell functionally expresses a chimeric HCN ion channel, wherein said chimeric HCN is hHCN212, and wherein the expressed chimeric HCN channel generates an effective pacemaker current when the cell is implanted into a subject's heart, and wherein the biological pacemaker comprises at least about 700,000 human adult mesenchymal QD-labeled MSCs.

Further, the present invention provides a tandem pacemaker system comprising (1) an electronic pacemaker, and (2) a bypass bridge comprising a strip of gap junction-coupled QD-labeled MSCs having a first end and a second end, both ends capable of being attached to two selected sites in a heart, so as to allow the transmission of an electrical signal across the tract between the two sites in the heart.

In a specific embodiment of the invention, the first end of the bypass bridge is capable of being attached to the atrium and the second end capable of being attached to the ventricle, so as to allow transmission of an electrical signal from the atrium to travel across the tract to excite the ventricle. Further, the QD-labeled MSCs of the bypass bridge can functionally express at least one protein selected from the group consisting of: a cardiac connexin; an alpha subunit and accessory subunits of a L-type calcium channel; an alpha subunit with or without the accessory subunits of a sodium channel; and a L-type calcium and/or sodium channel in combination with the alpha subunit of a potassium channel, with or without the accessory subunits of the potassium channel. Such cardiac connexins are selected from the group consisting of Cx43, Cx40, and Cx45.

Further, the present invention provides a tandem pacemaker system comprising (1) an electronic pacemaker, (2) a bypass bridge comprising a strip of gap junction-coupled QD-labeled MSCs having a first end and a second end, both ends capable of being attached to two selected sites in a heart, so as to allow the transmission of an electrical signal across the tract between the two sites in the heart, and (3) a biological pacemaker comprising comprises an implantable QD-labeled MSC that functionally expresses a (a) an HCN ion channel, or (b) a chimeric HCN channel wherein the chimeric HCN channel comprises portions of more than one type of HCN channel, or (c) a mutant HCN channel wherein the expressed HCN, chimeric HCN or mutant HCN channel generates an effective pacemaker current when said cell is implanted into a subject's heart. In an embodiment of the invention, the biological pacemaker of the tandem system, comprises at least about 200,000 QD-labeled MSCs. In another embodiment of the invention, the tandem pacemaker system comprises at least about 700,000 QD-labeled MSCs.

The present invention provides a method of treating a subject afflicted with a cardiac rhythm disorder, which method comprises administering a tandem pacemaker system as described herein to the subject, wherein the biological pacemaker comprising QD-labeled MSCs of the system is provided to the subjects heart to generate an effective biological pacemaker current and further providing the electronic pacemaker to the subject's heart to work in tandem with the biological pacemaker to treat the cardiac rhythm disorder. The electronic pacemaker may be provided before the biological pacemaker, simultaneously with the biological pacemaker or after the biological pacemaker. The biological pacemaker is designed to enhance beta-adrenergic responsiveness of the heart, decreases outward potassium current IKl, and/or increases inward current $I_f$.

Further, the biological pacemaker may be provided to the Bachman's bundle, sinoatrial node, atrioventricular junctional region, His branch, left or right bundle branch, Purkinke fibers, right or left atrial muscle or ventricular muscle of the subject's heart.

Cardiac rhythm disorders that may be treated using the tandem systems of the invention include, for example, sinus node dysfunction, sinus bradycardia, marginal pacemaker activity, sick sinus syndrome, tachyarrhythmia, sinus node reentry tachycardia, atrial tachycardia from an ectopic focus, atrial flutter, atrial fibrillation, bradyarrhythmia, or cardiac failure and wherein the biological pacemaker is administered to the left or right atrial muscle, sinoatrial node, or atrioventricular junctional region of the subject's heart.

In an embodiment of the invention, the electronic pacemaker is programmed to sense the subject's heart beating rate and to produce a pacemaker signal when the heart beating rate falls below a selected heart beating rate. The selected beating rate is a selected proportion of the beating rate experienced by the heart in a reference time interval. The reference time interval is an immediately preceding time period of selected duration.

The present invention provides a method of to a method of tracking the fate and distribution of QD-labeled MSCs utilized for treating a cardiac rhythm disorder, wherein the disorder is a conduction block, complete atrioventricular block, incomplete atrioventricular block, bundle branch block, cardiac failure, or a bradyarrhythmia, the method comprising administering a tandem pacemaker system comprising a bypass tract and an electronic pacemaker to the subject's heart such that the bypass tract spans the region exhibiting defective conductance, wherein transmission by the bypass tract of an electronic pacemaker current induced by the electronic pacemaker is effective to treat the subject, and wherein the electronic pacemaker is provided either prior to, simultaneously with or after the bypass tract is provided.

The present invention is also directed to a method of tracking the fate and distribution of QD-labeled MSCs utilized for treating a subject afflicted with a sinus node dysfunction, sinus bradycardia, marginal pacemaker activity, sick sinus syndrome, cardiac failure, tachyarrhythmia, sinus node reentry tachycardia, atrial tachycardia from an ectopic focus, atrial flutter, atrial fibrillation, or a bradyarrhythmia and a conduction block disorder, which method comprises (i) administering a tandem pacemaker system comprising a biological pacemaker composed of QD-labeled MSCs, a bypass tract and an electronic pacemaker, wherein an electronic pacemaker is provided either prior to, simultaneously with, or after the biological pacemaker is provided, and wherein the biological pacemaker is administered to the subject to generate an effective biological pacemaker current in the subject's heart, and wherein a bypass tract spans the region exhibiting defective conductance, wherein transmission by the bypass tract of an electronic pacemaker and/or biological pacemaker current is effective to treat the subject and (ii) determining the fate and distribution of the QD-labeled stem cells.

The present invention further relates to a method of tracking the fate and distribution of QD-labeled MSCs utilized for treating a subject afflicted with ventricular dyssynchrony comprising (a) selecting a site in a first ventricle of the subject's heart, (b) administering a biological pacemaker of as described herein to the selected site so as to initiate pacemaker activity and stimulate contraction of the first ventricle, (c) pacing a second ventricle of the heart with a first electronic pacemaker which is programmed to detect a signal from the biological pacemaker and to produce a pacemaker signal at a reference time interval after the biological pacemaker signal is detected, thereby providing biventricular pacemaker function to treat the subject (d) tracking the fate and distribution of the QD-labeled stem cells.

In a specific embodiment, the electronic pacemaker is further programmable to produce a pacemaker signal when it fails to detect a signal from the biological pacemaker after a time period of specified duration. Additionally, the system may further comprise a second electronic pacemaker to be administered to a coronary vein, wherein the second electronic pacemaker is programmable to detect a signal from the biological pacemaker and to produce a pacemaker signal in tandem with the first electronic pacemaker if said second electronic pacemaker fails to detect a signal from the biological pacemaker after a time period of specified duration, the first and second electronic pacemakers thereby providing biventricular function.

A tandem pacemaker system for treating a subject afflicted with ventricular dysynchrony is provided comprising (1) a biological pacemaker comprising QD-labeled MSCs to be administered to a first ventricle of the subject's heart, and (2) an electronic pacemaker to be administered to a second ventricle of the subject's heart, wherein the electronic pacemaker is programmable to detect a signal from the biological pacemaker and to produce a electronic pacemaker signal at a reference time interval after the biological pacemaker signal is detected, so as to thereby provide biventricular pacemaker function, and wherein the electronic pacemaker is provided either prior or simultaneously with the biological pacemaker.

Such a pacemaker system may further comprise a second electronic pacemaker to be administered to a coronary vein, wherein the second electronic pacemaker is programmable to detect a signal from the biological pacemaker and to produce a pacemaker signal in tandem with the first electronic pacemaker if said second electronic pacemaker fails to detect a signal from the biological pacemaker after a time period of specified duration, the first and second electronic pacemakers thereby providing biventricular function.

5.5. Uses and Administration of the Compositions of the Invention

The present invention provides methods and compositions which may be used to assess the safety and efficacy of treatments of various diseases associated with cardiac disorders. Specifically, through the use of QD-labeled MSCs, the fate and distribution of administered MSCs can be tracked. The term "cardiac disorder" as used herein refers to diseases that result from any impairment in the heart's pumping function. This includes, for example, impairments in contractility, impairments in ability to relax (sometimes referred to as diastolic dysfunction), abnormal or improper functioning of the heart's valves, diseases of the heart muscle (sometimes referred to as cardiomyopathy), diseases such as angina and myocardial ischemia and infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart (for example, atrial septal defect). For further discussion, see Braunwald, Heart Disease: a Textbook of Cardiovascular Medicine, 5th edition, W B Saunders Company, Philadelphia Pa. (1997) (hereinafter Braunwald). The term "cardiomyopathy" refers to any disease or dysfunction of the myocardium (heart muscle) in which the heart is abnormally enlarged, thickened and/or stiffened. As a result, the heart muscle's ability to pump blood is usually weakened. The disease or disorder can be, for example, inflammatory, metabolic, toxic, infiltrative, fibroplastic, hematological, genetic, or unknown in origin. There are two general types of cardiomyopathies: ischemic (resulting from a lack of oxygen) and nonischemic. Other diseases include congenital heart disease which is a heart-related problem that is present since birth and often as the heart is forming even before birth or diseases that result from myocardial injury which involves damage to the muscle or the myocardium in the wall of the heart as a result of disease or trauma. Myocardial injury can be attributed to many things such as, but not limited to, cardiomyopathy, myocardial infarction, or congenital heart disease. Specific cardiac disorders to be treated also include congestive heart failure, ventricular or atrial septal defect, congenital heart defect or ventricular aneurysm. The cardiac disorder may be pediatric in origin. The cardiac disorder may require ventricular reconstruction.

Cardiac rhythm disorders that may be treated include pathological arrhythmia, conduction block, complete atrioventricular block, incomplete atrioventricular block, bundle branch block, weak pacemaker activity, sinus node dysfunction, sinus bradycardia, sick sinus syndrome, bradydysrhythmia, tachydysrhythmia, SN re-entry tachycardia, atrial tachycardia from an ectopic focus, atrial flutter, atrial fibrillation, or cardiac failure. In another embodiment, a pre-existing source of pacemaker activity in the heart is ablated.

The methods of the invention comprise administration of QD-labeled MSCs in a pharmaceutically acceptable carrier, for treatment of cardiac disorders. "Administering" shall mean delivering in a manner which is affected or performed using any of the various methods and delivery systems known to those skilled in the art. Administering can be performed, for example, pericardially, intracardially, subepicardially, transendocardially, via implant, via catheter, intracoronarily, intravenously, intramuscularly, subcutaneously, parenterally, topically, orally, transmucosally, transdermally, intradermally, intraperitoneally, intrathecally, intralymphatically, intralesionally, epidurally, or by in vivo electroporation. Administering can also be performed, for example, once, a plurality of times, and/or over one or more extended periods.

QD-labeled MSC-based biological pacemakers may require focal delivery. Several methods to achieve focal delivery are feasible; for example, the use of catheters and needles, and/or growth on a matrix and a "glue." Whatever approach is selected, methods and compositions of the present invention provide a means for determining whether the delivered cells disperse from the target site. Such dispersion could introduce unwanted electrical effects within the heart or in other organs.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. The composition can be formulated as a suppository, with traditional binders and carriers such as triglycerides. Oral formulation can include standard carvers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical sciences" by E. W. Martin. Such compositions will contain a therapeutically effective amount of the therapeutic compound, preferably in purified form, together with a suitable amount of carrier so as to provide the form for proper administration to the patient. The formulation should suit the mode of administration.

The appropriate concentration of the composition of the invention which will be effective in the treatment of a particular cardiac disorder or condition will depend on the nature of the disorder or condition, and can be determined by one of skill in the art using standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

The present invention provides methods and compositions for tracking the fate and/or distribution of QD-labeled MSCs administered to a subject for treatment of a particular cardiac disorder or condition. Following administration of said cells using the methods outlined above, their distribution and fate may be determined using a variety of different methods well known to those of skill in the art. In a preferred embodiment of the invention tissue samples are removed from the treated subject to determine the spatial distribution of the QD-labeled cells. Removal of such samples may be performed, for example, surgically, at different time intervals following administration. In an embodiment of the invention the sample is removed from between 1 day to 2 months.

In an embodiment of the invention, tissue samples are removed from the treated subject and analyzed to determine the distribution and fate of the QD-labeled stem cells using routine histological methods. For microscopy, samples (histologic sections) are preferably immobilized on a solid support. Any solid support can be used, with exemplary solid supports including microscope slides, wall surfaces of reaction wells, test tubes, and cuvettes, and beads. The solid support can be formed of any material known to be suitable to those skilled in this art, including glass, polystyrene, polyethylene, polypropylene, and cross-linked polysaccharides. Preferably, the sample is fixed to a glass microscope slide. The sample can be fixed to the solid support by any suitable procedure, such as air-drying or chemical or heat treatment, that does not interfere with subsequent observation of the sample. It is preferred that the slide be immobilized in such a manner that it can be observed by light and fluorescence microscopy.

The prepared sample slides can be analyzed using known fluorescent techniques, such as fluorescent microscopy. For example, the sample can be viewed using a photomicroscope equipped with an ultraviolet (UV) source such as a mercury or xenon lamp and appropriate filters, and the images photographed using conventional techniques. The cells are illuminated with a UV light source, which is the source of excitation, and must be capable of producing specific wavelengths that can be used to excite the QD-labeled cells of the invention.

In a preferred embodiment of the invention, custom filters may be used to preferentially excite the QDs at a wavelength of emitted light. This is possible because QDs have a large Stokes shift, i.e., distance between wavelength of excitation and wavelength of emission, whereas this is not possible with traditional fluorophores because of the closeness in peaks of excitation and emission and the overlap in these spectra. The custom filters are designed to collect a very narrow beam of emitted light at the peak of the spectrum, so any light coming from auto-fluorescence is exclude. QD-MSCs can also be detected using flow cytometry and labeled cells can be sorted using fluorescence activated cell sorting (FACS).

In a specific embodiment of the invention, the spatial locations of QD labeled cells can be identified and from a series of binary maps visualized in 3-D. For reconstructing the 3-D distribution of injected QD-hMSCs, tissue is processed as serial transverse 10-μm-thick sections and imaged for both QD (655-nm) fluorescence and phase contrast on the Axiovert deconvolution microscope with the 2.5× objective. Using Axiovision software, fluorescence and phase images for each section are merged to generate jpg images. The remaining image processing is executed in Matlab. The lines of code are attached as Table I. Phase contrast features echoed in each serial section are identified and the coordinates are used to spatially register the images with respect to one another. These registered RGB jpgs are converted to HSV format and the saturation and value channels are used to create new intensity images bearing only the QD-positive regions. The images are then thresholded to generate binary maps, where white pixels represent all of the QD-positive zones. The binary maps for all of the serial sections are combined into a 3-D matrix, and the total area (or volume) of white pixels is computed. High-resolution images (63×) are obtained and areas of single cells are determined. Thus, the number of cells in the reconstruction is calculated by dividing the total 3-D area by the average area of QDs per cell in a section. The centroid is determined for each individual polygon in the volume matrix, and then weighted to the polygon volume to find the centroid of the total cell mass. Next, the distance is calculated between each individual cluster and the centroid of the cell mass to characterize the distribution of QD-hMSCs in the tissue. The distribution is visualized in 3-D by extracting isosurface data from the volume matrix and composing patch graphics objects for each of the continuous polygons in the matrix.

In yet another embodiment of the invention, QD-labeled cells may be detected in vivo using micro-Computer Tomography (μCT) Scanning.

Additionally, the progress of the recipient receiving the treatment may be determined using assays that are designed to test cardiac function. Such assays include, but are not limited to ejection fraction and diastolic volume (e.g., echocardiography), PET scan, CT scan, angiography, 6-minute walk test, exercise tolerance and NYHA classification.

6. EXAMPLE

Biological Features of QD Labeled Mesenchymal Stem Cells

The experiments described below include in vitro validation of hMSC loading with QDs, in vivo delivery of QD-hMSCs to rat and canine hearts, and development of custom computer algorithms to reconstruct the 3-D distribution of hMSCs in vivo.

6.1 Material and Methods

Computer Algorithms. Custom algorithms were designed and executed in Matlab 6.5 and 7.0 (MathWorks, Natick, Mass.). Images were obtained on the Zeiss Axiovert microscope using the 2×, 10×, or 63× objective and 655-nm custom filter set described above, and then converted to jpg using Axiovision software (ver 4.3, Carl Zeiss Vision, Germany). For QD cluster analysis, QD fluorescence intensity images (63×) were obtained from cells at various time points after loading. Images were thresholded based on Otsu's method, to minimize the intraclass variance between black and white pixels. The individual binary image clusters were identified and their major axis lengths were determined in order to calculate cluster diameters. Corresponding nuclear images of Hoechst 33342 staining were used to compute the number of cells in the image fields. Finally, the number of QD clusters per cell was calculated for each time point.

A routine was developed for reconstructing the 3-D distribution of QD-hMSCs injected into rat hearts. Tissue was processed as described above and 222 (rat terminated at 1 hour) or 126 (rat terminated at 1 day) serial transverse 10-μm-thick sections were imaged for both QD (655-nm) fluorescence and phase contrast on the Axiovert deconvolution microscope with the 2.5× objective. Using Axiovision software, fluorescence and phase images for each section were merged to generate jpg images. The remaining image processing was executed in Matlab. Phase contrast features echoed in each serial section were identified and the coordinates were used to spatially register the images with respect to one another. These registered RGB jpgs were converted to HSV format and the saturation and value channels were used to create new intensity images bearing only the QD-positive regions. These were then thresholded to generate binary maps, where white pixels represent all of the QD-positive zones. All of the QD-positive cells that were not contained within the cardiac syncytium (cells remaining in the adhesive on the epicardial surface) were eliminated from the reconstructions. The binary maps for all of the serial sections were combined into a 3-D matrix, and the total area (or volume) of white pixels was computed. High-resolution images (63×) were obtained and areas of single cells were determined similar to the method described above. Thus, the number of cells in the reconstruction was calculated by dividing the total 3-D area by the average area of QDs per cell in a section. The centroid was determined for each individual polygon in the volume matrix, and then weighted to the polygon volume to find the centroid of the total cell mass. Next, the distance was calculated between each individual cluster and the centroid of the cell mass to characterize the distribution of QD-hMSCs in the tissue. The distribution was visualized in 3-D by extracting isosurface data from the volume matrix and composing patch graphics objects for each of the continuous polygons in the matrix.

Cell culture. Human mesenchymal stem cells (hMSCs) were obtained from Clonetics/Biohittaker (Walkersville, Md.) and passages p3-p7 were used for all in vitro and in vivo experiments. Cells were grown on polystyrene tissue culture dishes and maintained at 37° C. in humidified 5% $CO_2$ in Mesenchymal Stem Cell Growth Media supplemented with L-glutamine, penicillin and serum (MSCGM BulletKit, Cambrex). Cells were re-plated for passaging once every two weeks. For isolation of canine cardiac myocytes, adult mongrel dogs were intravenously injected with 80 mg/kg body weight sodium pentobarbital according to an approved protocol. Hearts were then removed and placed in a cold, high-potassium Tyrode solution [16]. Myocytes were isolated using a modified Langendorff system with digestion via Worthington type II collagenase [17], cultured onto laminin-coated glass coverslips and maintained in Dulbecco's Modified Eagle Medium (DMEM) with 1% penicillin/streptomycin.

Quantum dot loading. Three approaches were used for loading hMSCs with QDs. First, a nucleofection protocol was followed to electroporate approximately $5\times10^5$ hMSCs in 8.2 nM QDs (Qdot 655 ITK Carboxyl Quantum Dots, Invitrogen Cat. No. Q21321MP) solution (supplemented Human MSC Nucleofector Solution, Amaxa Biosystems, Cat. No. VPE-1001). After electroporation, cells were re-plated in complete MSCGM media onto polystyrene tissue culture dishes. Second, a commercially available kit was used to load the cells with QDs via a carrier protein (Qtracker 655 Cell Labeling Kit, Invitrogen Cat. No. Q25021MP). Briefly, 10 nM of labeling solution was prepared according to kit directions, and approximately 0.2 mL was added to a 100-mm polystyrene tissue culture dish containing roughly $5\times10^5$ cells. The cells were incubated at 37° C. for 45-60 minutes, after which time they were washed twice with complete MSCGM. The third (and optimal) loading technique will be referred to as passive loading. Cells were grown to 85% confluence on polystyrene tissue culture dishes. An 8.2 nM solution of 655 ITK Carboxyl QDs was prepared in complete MSCGM and vortexed for 60 seconds. Cells were washed once in phosphate-buffered saline (PBS) and incubated in the QD solution for up to 24 hours at 37° C.

Quantum dot validation and mechanistic experiments. After the incubation period, cells were washed twice in PBS and fresh MSCGM was replaced. Loading efficiency was analyzed visually from a set of images of QD-hMSCs as well as by flow cytometry. In the first method, 181 cells from four QD fluorescence and phase contrast overlay images were studied and identified as either QD-positive or negative. Loading determination via flow cytometry was assessed using the following protocol: hMSCs were loaded with QDs for 24 hours as described above. After the loading period, cells were washed twice in PBS, trypsinized and resuspended in PBS with 5% FBS. Cells were then stained with 7-amino-actinomycin D (to determine viability) and subsequently analyzed using a LSR II true multiparameter flow cytometer analyzer (BD Biosciences with custom 655-nm filter). Four sets of QD-hMSCs (and unloaded hMSCs for control), each containing a minimum of 17,000 cells, were analyzed. The intensity range for control cells was set such as to include at least 98% of the viable cells. The same technique was used to scan the QD-hMSCs and determinations of QD-positive status were based on viable cells in the intensity range above that set for control.

A number of additional in vitro experiments were performed. To determine the degree of loading after repeated cell divisions, cells were passaged three times at 1:4 for a minimum of 5 divisions over 44 days. For one set of experiments intended to determine the mechanism of loading, hMSCs were passively exposed to QD incubation medium for 7 hours at either 4° C. or 37° C. In another approach, cells were passively exposed to QD incubation medium for 12 hours either in MSCGM or 125 μM colchicine (Sigma, Prod No C9754) in MSCGM. To determine if canine cardiac myocytes (cCMs) would take up QDs, cultured myocytes were incubated for up to 24 hours in DMEM to which the lysate from approximately $10^4$ QD-hMSCs was added.

Proliferation assay. A population of hMSCs was evenly split for passaging and both dishes were grown to ~85% confluence. One dish was passively loaded with QDs as described above while the other received a media exchange.

The following day (after 24 hours of loading), both dishes were washed and re-plated at equal concentrations into 12 wells each of a 96-well dish and cells were allowed to grow for 3 days. The mitochondrial dehydrogenase assay (MDA, KKBiomed) was carried out according to instructions provided by the company. The absorbance of each of the samples was measured at 595-nm using a Polarstar OPTIMA microplate reader (BMG Technologies).

Differentiation experiments. Induction was performed using adipogenic, chondrogenic and osteogenic kits available through Cambrex (Adipogenic Differentiation Medium, PT-3004; Chondrogenic Differentiation Medium, PT-3003; Osteogenic Differentiation Medium, PT-3002). All experiments were performed in triplicate on both QD-hMSCs and hMSCs. For adipogenesis, labeled and unlabeled cells were plated at $2\times10^4$ cells/cm$^2$ tissue culture surface area and fed every 2-3 days with MSCGM until cultures reached 100% confluence (5-13 days). Cells were fed on the following regime for a total of 3 cycles: 3 days with supplemented Adipogenic Induction Medium followed by 1-3 days with Adipogenic Maintenance Medium. Control hMSCs were fed with Adipogenic Maintenance Medium at all times. After the 3 cycles, all cells were cultured for another week in Adipogenic Maintenanc Medium. Cells were analyzed using light microscopy for characteristic lipid vacuole formation. Matlab algorithms were designed to determine percent of images occupied by adipocytes. For osteogenesis, cells were plated at $3\times10^3$ cells/cm$^2$ tissue culture surface area and cultured overnight in MSCGM. Cells were then fed with Osteogenesis Induction Medium with replacement media every 3-4 days for 2-3 weeks. Non-induced control cells were fed with MSCGM on the same schedule. Cells were analyzed using light microscopy for characteristic cobblestone appearance.

Gene transfections. For some experiments, hMSCs were transfected with pIRES-EGFP (4 µg, FIG. 3), HCN2-pIRES-EGFP (4 µg, FIG. 3), or Wnt5A (4 µg, pUSEamp, Upstate Cell Signaling Solutions, FIG. 4) plasmids using the Amaxa biosystems nucleofection technique[10].

Patch clamping. Whole cell patch clamping was executed as previously described [10]. Patch electrode resistance was 4 to 6 MΩ. The pipette solution was filled with (in mM) K-aspartate 120, Mg-ATP 3, EGTA 10, and HEPES 5 (pH adjusted to 7.2 with KOH). The external solution contained (in mM) NaCl 137.7, KCl 5.4, NaOH 2.3, CaCl$_2$ 1.8, MgCl$_2$ 1, Glucose 10, and HEPES 5 (pH adjusted to 7.4 with NaOH). Recordings were made at room temperature.

Visualization of QD-hMSCs. In vitro experiments were performed in polystyrene tissue culture dishes. For typical visualization, cells were re-plated onto CC2-coated glass chamber slides (Lab-Tek). Several hours after re-plating, slides were rinsed in PBS and then fixed in 4% paraformaldehyde (PFA) for 15 minutes. Slides were rinsed again in PBS for 5 minutes, and then incubated in 1 µM Hoechst 33342 nuclear dye (Cambrex) for 20 minutes. They were then washed in PBS for 5 minutes and placed in dH$_2$O for 20-30 seconds. The slides were rinsed successively in 30%, 70%, 95% and 100% ethanol each for 30 seconds and then placed in 100% toluene for 30 seconds. Finally, slides were mounted in CytosealTM60 (Electron Microscopy Systems) containing 1% triocytylphosphine (TOP, Sigma), with coverslips allowed to set overnight. Images were acquired on an inverted Zeiss Axiovert deconvolution microscope with AxioCam MRm CCD camera using a filter customized for 655-nm QD emission (Omega Optical, XF3305, excitation at approximately 420-nm); the DAPI filter set was used to visualize Hoecsht 33342-stained nuclei. For some images, z-stacks were obtained at multiple focal planes and subsequently deconvolved using AxioVision (ver 4.3, Carl Zeiss Vision, Germany). These stacks were then reassembled (using the same software) into single 2-D images based on fluorescent pixels deemed most in plane at each section. All additional image processing was carried out using custom Matlab algorithms (Matlab 6.5 and 7.0, MathWorks, Natick, Mass.) or in ImageJ (ver 1.32j, NIH). For some experiments, imaging was performed on live cells using an Olympus inverted fluorescence microscope (Olympus IX51, DP70 camera) with GFP and Texas Red (for QD imaging) filter sets.

In vivo Studies. All animals received humane care in compliance with the Principles of Labroatory Animal Care formulated by the National Society for Medical Research and the Guide for the Care and Use of Laboratory Animals prepared by the National Academy of Sciences and published by the National Institutes of Health (NIH Publication No. 85-23, revised 1985).

Patch preparation. hMSCs were loaded with QDs as described above and subsequently transfected with the Wnt5A plasmid. A 15×30×0.1 mm acellular ECM patch (porcine urinary bladder matrix, ACell, Jessup, Md.) was rinsed twice in PBS for 10 minutes each. The patch was then soaked in MSCGM for 15 minutes, after which time the media was removed. QD-Wnt5A-hMSCs were trypsinized, resuspended in MSCGM and seeded directly onto the ECM. The patch was returned to 37° C. for approximately 12 hours prior to implantation.

Canine patch implants. Patches were implanted as described previously [18]. Briefly, a thoracotomy was used to expose the heart. A vascular clamp was then used to isolate a region of the right ventricular free wall. A full thickness defect was surgically induced and an hMSC-seeded scaffold was used to replace it. The chest was closed and the animal was allowed to recover. Animals were sustained under veterinary care and humanely terminated by an approved protocol at 8 weeks with pentobarbital.

Rat heart injections. QD-hMSCs were prepared as described above. 24 hours after QD incubation, cells were washed twice in PBS, trypsinized and re-suspended for a final cell concentration of approximately $10^5$ cells/10 µL in DMEM at 4° C. The cell solution was stored on ice until injection. Rats (5-months-old, Charles River) were anesthetized with ketamine/xylazine intraperitoneally, intubated and maintained on inhaled isofluorane (1.5-2%) for the duration of the experiment. A left thoracotomy was performed at the 4th or 5th intercostal space. A 5-0 prolene suture was used to place a superficial stitch in the epicardium as a fiducial marker. 10 µL of cell solution or cell lysate was injected into the free left ventricular wall apical to the suture and then a small drop of surgical grade tissue adhesive (Nexaband, JA Webster) was applied over the injection site. The thorax was closed and rats were returned to their cages for either 1 hour or 1 day for whole cell injections, or either 1 hour or 1 week for the lysed QD-hMSC injections. Euthanasia was performed either in a $CO^2$ chamber or by administering pentobarbital (100 mg/kg body weight injected intraperitoneally) and subsequent cardiectomy.

Preparation of tissue samples. Immediately after explantation, tissue samples were rinsed in isotonic saline and then fixed in 4% PFA for 24 hours. After fixation, tissue was cryopreserved in an isotonic 30% sucrose solution for at least 24 hours. Gross photographs were obtained of tissue samples with sutures in situ to identify the cell delivery zone (either patch borders or injection site). After suture removal, tissue was embedded in freezing matrix (Jung tissue embedding matrix, Leica) and stored at −20° C. 10-µm tissue sections were cut on a cryotome, transferred to Suprafrost glass slides and stored at −20° C. Slides were either imaged without mounting, or stained with Hoechst 33342 dye and mounted as described above.

Immunohistochemistry. Staining for CD31 was performed as follows: 10-μm histologic sections were hydrated with PBS, and permeablized with 0.5% Tween-20 in 1×TBS followed by 0.25% Triton X-100 in TBS. Samples were blocked with normal horse serum (Vector, Burlingame, Calif.) and then incubated for 3 hours in FITC-conjugated anti-human CD31 (Diaclone, Stamford, Conn.). Control sections were incubated in PBS instead of the antibody. Sections were washed in PBS, incubated with 1□M Hoescht33342 for 20 minutes (Invitrogen, Carlsbad, Calif.), then washed in PBS before mounting with Vectashield (Vector, Burlingame, Calif.).

Statistics. All data are listed as mean±standard deviation. Data sets were compared by a Student's t-test with p<0.05 considered significant.

6.2. Results

Figure 1B:
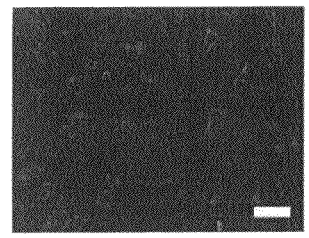
Figure 1C:
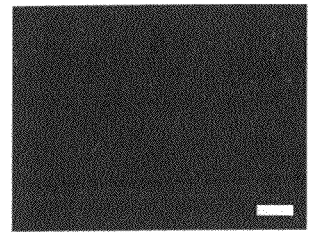
Figure 1D:
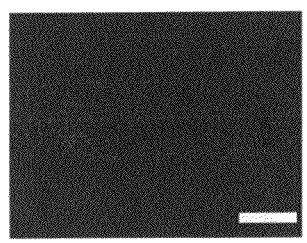
Figure 1E:
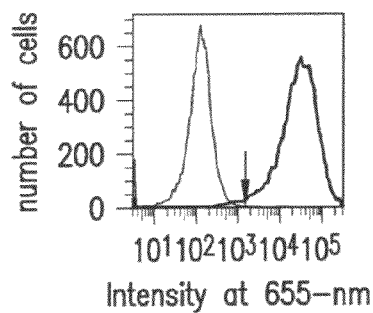
Figure 1F:
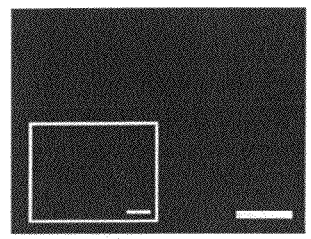
Figure 1G:
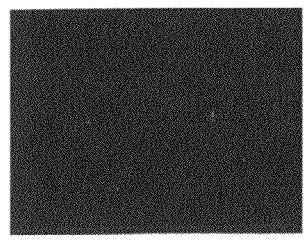
Figure 1H:
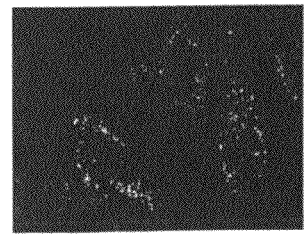
Figure 1I:
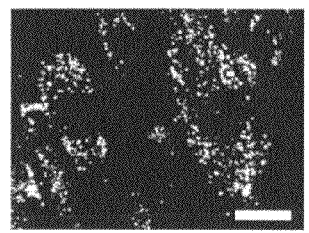

Loading of hMSCs is optimized by passive incubation with negatively charged QDs and is blocked by inhibitors of endocytosis. Optimal use of QDs for tracking hMSCs requires nearly 100% cell survival after loading and that loaded cells behave similarly to unloaded cells. Potential approaches to loading populations of cells include electroporation[19], lipid vehicles[19-21] and passive (receptor-mediated or unmediated) incubation[22-27]. Loading using QDs with either positively or negatively-charged surface conjugations was examined using these methods. Electroporation was least effective, loading only a small fraction of the hMSC population and causing appreciable cell death. Receptor-mediated uptake was more effective (FIG. 1A) but still non-uniform. Unfortunately, both methods resulted in marked aggregation of the QDs in the perinuclear spaces of the hMSCs over time. Passive incubation with naked QDs (655-nm peak emission wavelength) having carboxylic acid derivitizations on their polymer surfaces (net negatively charged) was most effective (FIGS. 1B, 1C). The pattern of loading was diffusely cytoplasmic (FIG. 1D). Virtually all hMSCs were loaded (>98% of 181 cells analyzed visually in four images and >96% of >17,000 cells per set analyzed by flow cytometry, N=4 sets, FIG. 1E). When incubations were attempted using smaller-core-sized QDs (525-nm peak emission wavelength) with either positively or negatively-charged surface conjugations, similar levels of loading where not achieved. The mechanism of QD loading was investigated by employing two protocols that reduce endocytosis: exposure to low temperature for 7 hours (4° C.) and application of colchicine (125 μM, an inhibitor of microtubule aggregation [28]) for 24 hours prior to and during incubation with QDs (FIG. 1F). In each case there was a dramatic reduction in QD uptake. Finally, the time course of QD loading was investigated by passively incubating cells with QDs for 1, 3, 7, 12 and 24 hours. Intracellular QDs were barely detectable at 1 hour of incubation (FIG. 1G), easily detectable after 3 hours (FIG. 1H) and quite bright at 24 hours (FIG. 1I), prompting us to choose an incubation range of 12-24 hours for most experiments.

Table 1 represents a summary of loading conditions. Attempts were made to load hMSCs by testing combinations of various parameters (listed at top). Negatively-charged dots had carboxylated surface derivitizations. Positively-charged dots had additional amino-PEGylation coatings on the surface. Some dots had additional streptavidin molecules conjugated to the polymer surface resulting in either net negatively-charged or neutral dots. Loading with QDs of larger core sizes (proportional to wavelengths of emission of 655-nm and 800-nm) was successful whereas loading with smaller dots (green, 525-nm) yielded much lower uptake. The most important variables for uniform and complete loading were: (1) surface charge, (2) core size, and (3) incubation media.

Figure 2C:
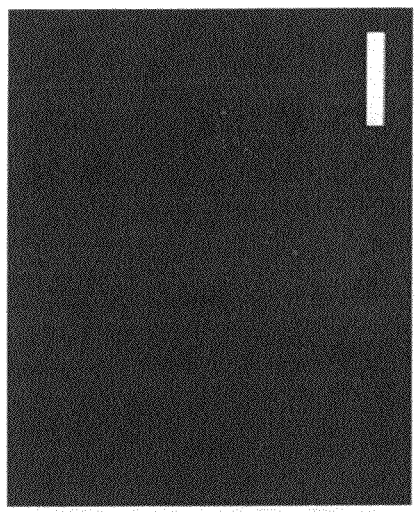
Figure 2B:
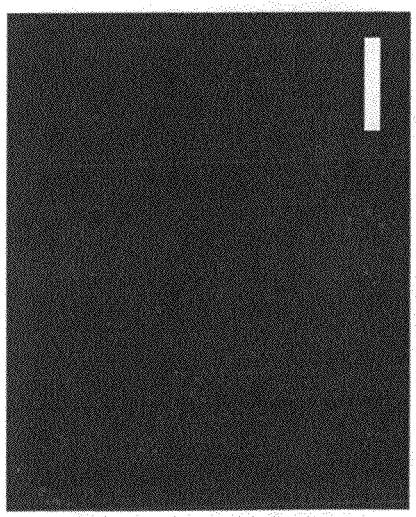
Figure 2A:
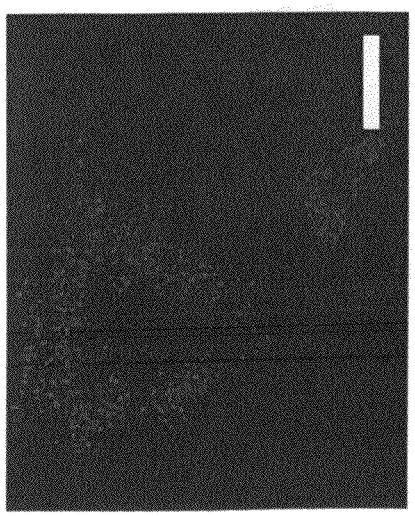
Figure 2F:
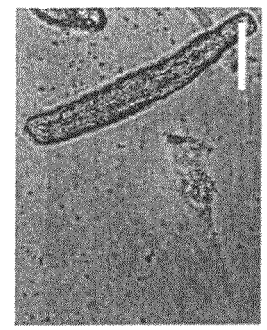
Figure 2E:
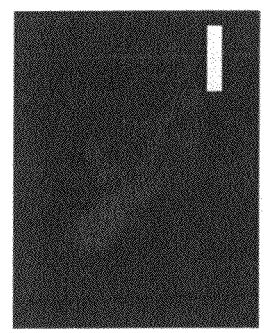
Figure 2D:
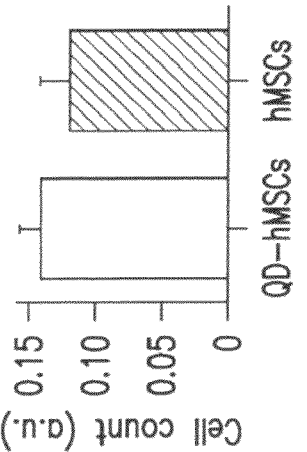

QD-loaded hMSCs continue to proliferate and retain label for more than 6 weeks in vitro. To be useful for stem cell tracking, intracellular QDs must not interfere with cellular function or proliferation. QD-hMSCs were studied for up to 44 days in vitro. During this time period the cells divided at least five times (consistent with the proliferative behavior of unloaded hMSCs, see below) and retained sufficient label to be easily imaged (FIG. 2A-C). The intracellular QD cluster sizes were stable over this period (0.84±0.11 μm, 0.91±0.21 μm, 0.94±0.13 μm, average cluster diameters for 2, 16 and 44 days after loading respectively) and the distribution remained cytoplasmically diffuse. As shown in FIG. 2D, a proliferation assay on QD-hMSCs and plain hMSCs revealed no difference between the two groups (0.1405±0.0165 a.u. vs. 0.1186±0.0230 a.u. respectively, p>0.05, N=12 per group).

QDs do not transfer to adjacent cells. To prevent the occurrence of false positives, a tracking agent must not transfer from labeled to unlabeled stem cells. The only direct path of contact between the intracellular space of one cell and that of another is the gap junction channel. It was previously demonstrated that hMSCs express connexins 43 and 40 and form functional gap junctions when placed in close apposition[29]. An experiment was designed to investigate possible transfer of QDs from loaded to unloaded hMSCs. QD-hMSCs were co-cultured with hMSCs transfected to express green fluorescent protein (GFP-hMSCs). The co-culture was grown to near confluence and GFP-hMSCs in close proximity to QD-hMSCs were imaged, as depicted in FIG. 2E.

No evidence of internalized QDs in GFP cells was observed in four experiments. This is consistent with the known diameters of QDs (~10 nm) and gap junction channels (~1 nm).

QDs are not taken up by adult cardiac myocytes in culture. hMSCs have been shown to enhance cardiac regeneration in animal trials[4]. If QDs are used to track the fate of stem cells delivered to the heart, myocytes must not take the dots up from the extracellular space should these exogenous cells die in their vicinity. To simulate the in vivo situation of dying hMSCs, cultured cardiac myocytes were exposed to the cell lysate from mechanically disrupted QD-hMSCs for 24 hours. FIG. 2F provides one example, demonstrating that the myocytes did not take up QDs. An equivalent control was performed using lysed cells in vivo, which is discussed below.

Figure 3A:
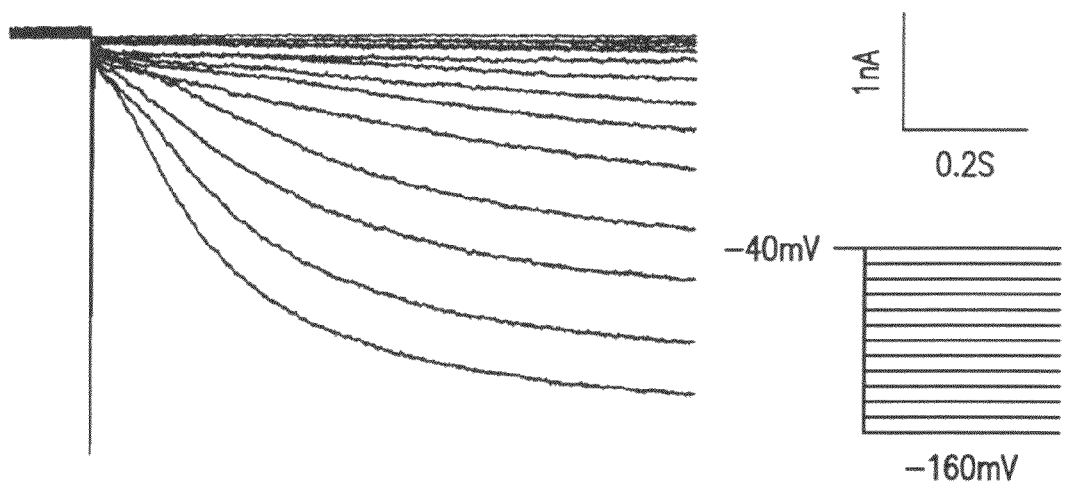
Figure 3B:
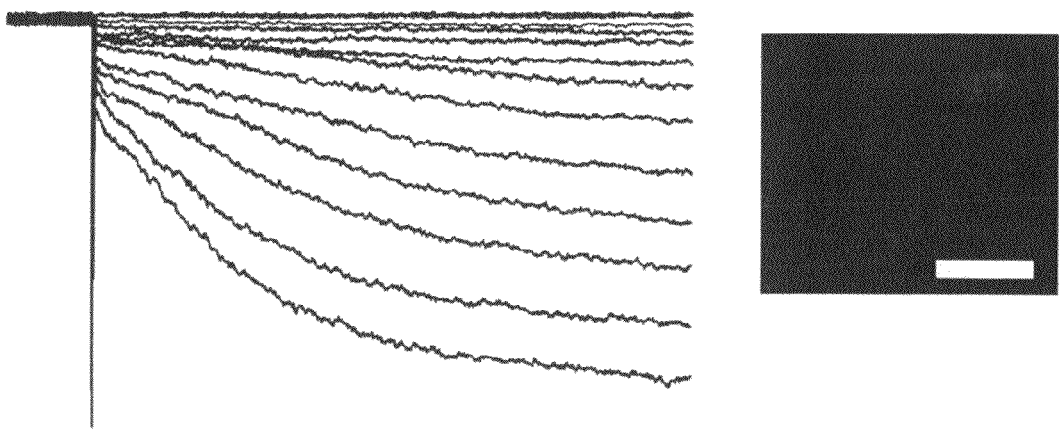

QD-loaded hMSCs can be transfected to overexpress genes. Because hMSCs are an attractive vehicle for gene delivery to the heart[10], it was investigated whether the presence of intracellular QDs would affect expression of exogenous genes. QD-hMSCs were transfected with the HCN2-pIRES-EGFP plasmid. The HCN2 gene expresses a time dependent inward current, which is the basis of cardiac pacemaker activity. This plasmid was previously used with hMSCs as the cellular vehicle to create a biological pacemaker in the canine heart[10]. After 48 hours, QD-loaded cells were visualized for GFP expression and compared to control hMSCs that underwent the same transfection protocol but were not first exposed to QDs. GFP-positive cells from each group were then selected for patch clamping to record membrane currents (FIGS. 3a and 3b). QD-hMSCs expressed the HCN2 gene and generated a family of pacemaker currents similar to those recorded in unloaded cells. The current amplitudes recorded at −150 mV for both control and QDhMSCs were −1459.48±616.83 and −1352.68±864.70 respectively (p>0.05, N=5 per group).

Figure 5F:
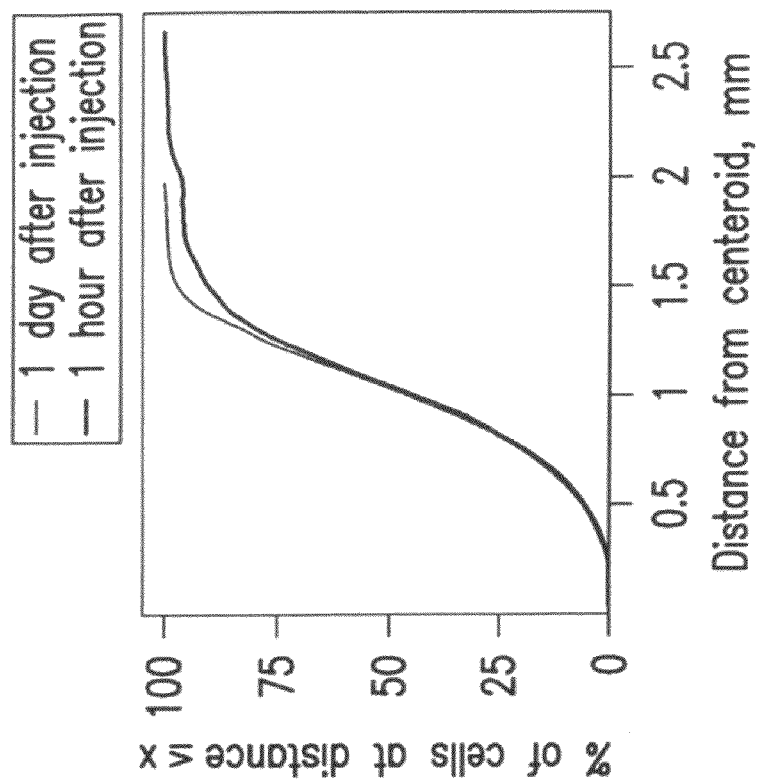

Intracellular QDs do not interfere with differentiation potential of hMSCs in vitro. hMSCs are one of several stem cell types being studied for use in tissue repair and regeneration. We queried whether the presence of intracellular QDs would affect the ability of hMSCs to differentiate along mesodermal lineages. We cultured QD-loaded and unloaded hMSCs under conditions of adipogenesis or osteogenesis. After 23 days of adipogenic induction, both unloaded and QD-loaded hMSCs showed similar levels of differentiation (44.9% and 40.4% area occupied by adipocytes respectively for fields of view shown in FIGS. 5a and b). Furthermore, terminally differentiated adipocytes originating from QD-loaded hMSCs retained the QD label (FIG. 5c). Both unloaded and QD-loaded hMSCs responded to the osteogenic induction similarly, with both groups of cells showing characteristic changes in morphology from spindle shaped to cobblestone shaped and tendency toward clustering by day 15 (FIGS. 5d and e respectively). Again, cobblestone-shaped osteocytes derived from QD-hMSCs still contained QDs at the end of the differentiation process (FIG. 5f).

Figure 4B:
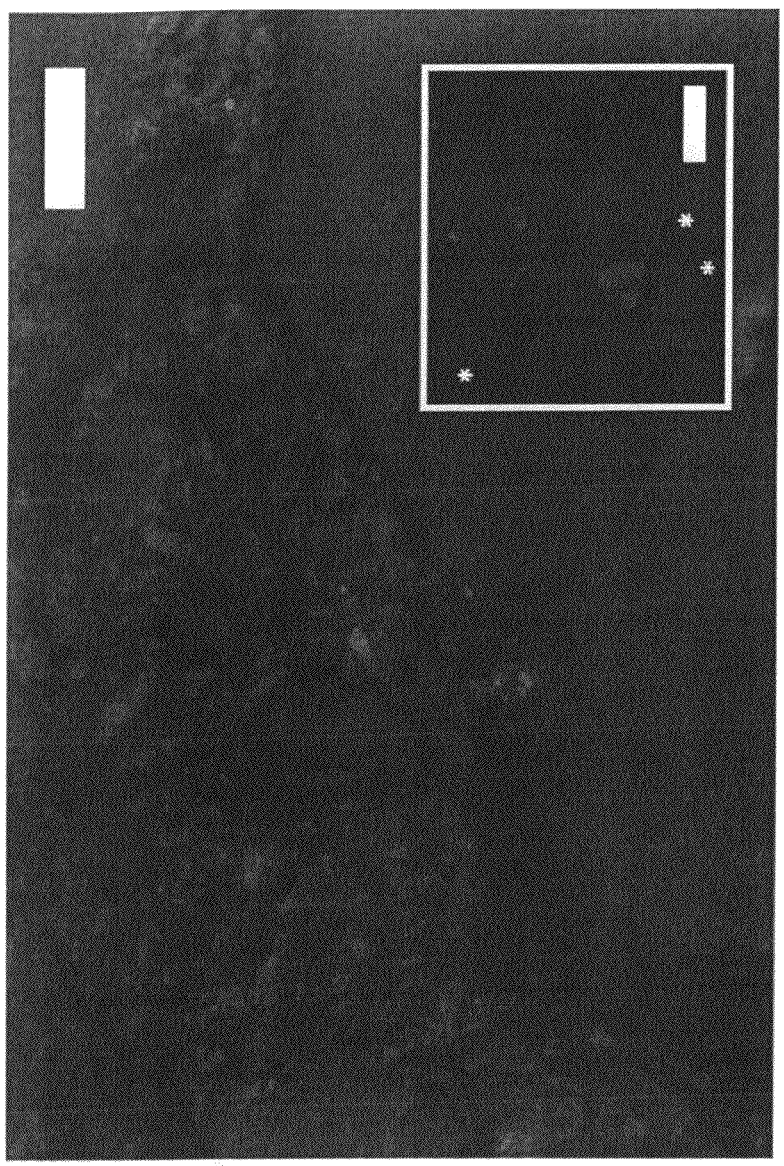
Figure 4A:
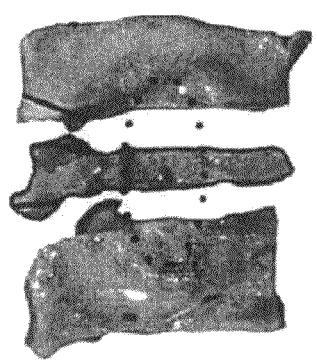
Figure 4C:

QD-hMSCs can be implanted into canine ventricle and identified up to 8 weeks later. Both cellular and functional cardiac regeneration was previously observed after replacing a full thickness right ventricular defect in the canine heart with an acellular extracellular matrix (ECM) patch derived from porcine urinary bladder[18]. If a naked ECM patch induces regeneration it might be possible to enhance the regeneration process by delivering hMSCs on a patch. Therefore, ECM patches (~15×30×0.1 mm) seeded with QD-hMSCs were implanted, the animals were terminated 8 weeks after implantation and a region of myocardium circumscribing the patch implant area was excised (FIGS. 4A and 4C). Transmural sections (10-μm) within the patch region were imaged to identify QD-hMSCs (FIG. 4B). FIG. 4B illustrates that QD fluorescence can be imaged in tissue without any detectable contribution from background autofluorescence. Further, individual hMSCs can be easily imaged and continue to display a diffuse cytoplasmic pattern of QD fluorescence (FIG. 4B, inset).

QDs do not affect differentiation of hMSCs in vivo. hMSCs have been found to spontaneously differentiate along an endothelial lineage and participate in angiogenesis in response to tissue injury[31]. We sought to determine whether the presence of QDs in these cells would affect their ability to develop an endothelial fate. Histologic sections from the 8-week QD-hMSC ECM patch explant were stained for the marker CD31 (PECAM-1) using a human-specific antibody. Many of the QD-containing regions in these sections stained positively for CD31 (FIG. 5g), with several areas showing clear co-localization (FIG. 5g inset), suggesting that these cells were differentiating along an endothelial lineage. As a means of control, endogenous canine endothelium from the same tissue sections were negative for the marker (FIG. 5h), as were cultured hMSCs in vitro (FIG. 5j), whereas human endothelial cells in culture stained positively (FIG. 5i).

QDs are not internalized by cardiac cells in vivo. A set of experiments were performed to determine whether native myocardial cells internalize QDs in vivo. QDs can exist extracellularly if QD-hMSCs die and leak their contents. Therefore, a suspension of approximately 100,000 QD-hMSCs that were mechanically disrupted to cause cell lysis were injected into the rat ventricle and the animals were terminated at either 1 hour (N=2) or 1 week (N=2). QDs were not observed in any cell type in these hearts. This finding is expected, as free carboxylated QDs will be removed by the reticuloendothelial system in less than one hour[31].

Figure 5E:
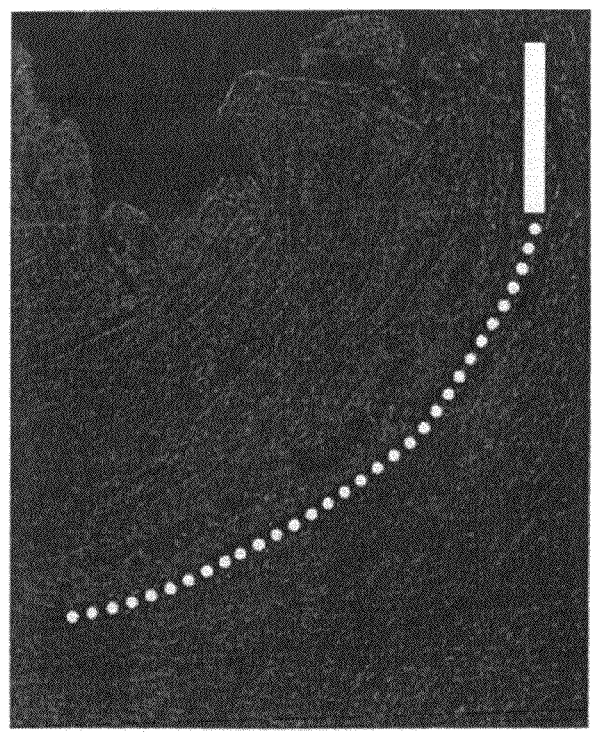
Figure 6A:
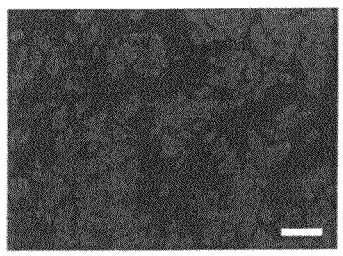
Figure 6B:
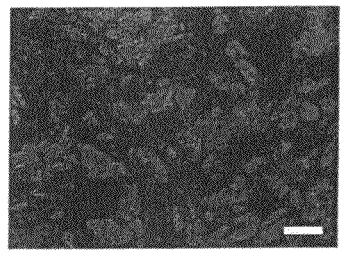
Figure 6C:
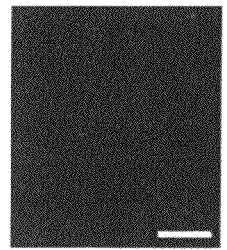
Figure 6D:
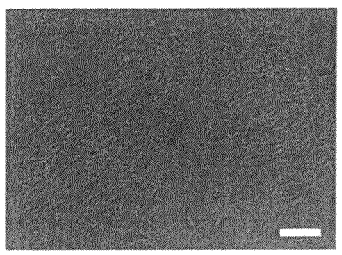
Figure 6E:
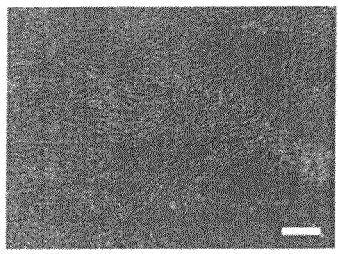
Figure 6F:
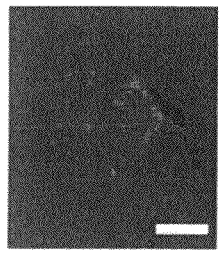
Figure 6G:
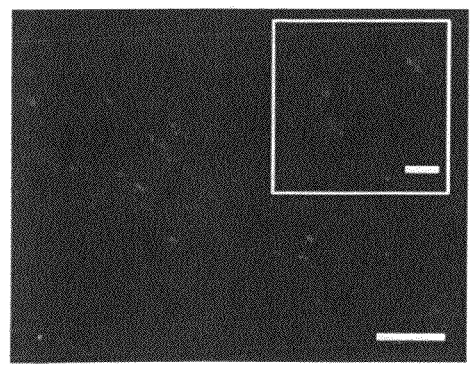

The number and distribution of QD-hMSCs injected into a rat heart can be reconstructed in 3-D. One million hMSCs had previously been injected into canine myocardium to create a biological pacemaker and traditional means of identifying these cells in histologic sections were used (GFP and secondary staining)[10]. Although it was possible to demonstrate the presence of some of our delivered cells, it was not possible to reconstruct their three-dimensional locations. Such added information could help to understand how these HCN2-transfected stem cells generated pacemaker activity and to assess their potential to develop unwanted arrhythmic events. With this need in mind, a series of experiments were performed in rats to enumerate delivered cells in vivo and reconstruct their spatial distribution in three dimensions. Approximately 100,000 QD-hMSCs were injected into the left ventricular free wall. Hearts were harvested at either 1 hour or 1 day after injection. Serial 10-μm transverse sections were imaged for QD fluorescence (FIGS. 5A and 5E). Using algorithms described in Supplementary Methods, these fluorescence images were filtered and thresholded to generate binary maps of QD-positive zones from all of the tissue sections (FIG. 5B). The spatial locations of QD-hMSCs were identified from the series of binary maps and visualized in 3-D (FIGS. 5C and 5D). The algorithms described herein permit enumeration of the total number of QD-hMSCs in the whole heart from these models (approximately 50,000 at 1 hour and 30,000 at 1 day). A distance parameter was also computed to characterize the distribution of cells, based on the distance between individual cells and the centroid of the total stem cell mass. Most of the cells were clustered in close proximity (85% of cells within 1.5 mm at 1 hour and 95% within 1.5 mm at 24 hours, see FIG. 5E).

Computer Tomography (CT) Scanning of QDs. QDs are semiconductor nanoparticles comprised of a CdSe core and ZnS shell. Because of the very high densities of these materials (5.816 g/cm$^3$ and 4.09 g/cm$^3$ respectively), it was investigated whether QD-hMSCs could be imaged using computed tomography (CT) scanning. In order for QD-hMSCs to be detected within a block of tissue, two criteria must be satisfied: 1) the resolution of the CT scanner must be sensitive enough to detect single cells (mean diameter, 10 μm) and 2) the overall physical density of a QD-loaded hMSC must be at least 10% higher than the physical density of the surrounding tissue. Currently, micro CT (μCT) scanners are available with resolutions as low as 1 μm.

After uptake by hMSCs, QDs exist within the cells in clusters with an average diameter of 0.75 μm. Prior to cell division the average cell contains approximately 200 of these QD clusters, as determined by fluorescence imaging. Since an individual cluster will occupy approximately 0.22 μm$^3$ in the cell, the total volume of QDs in a given cell is roughly 44 μm$^3$. An average hMSC has a volume of approximately 500 μm$^3$. Therefore, based on these calculations, QDs occupy approximately 9% of the volume of the cell. This is a low-end estimate of the percent volume, with alternate calculations yielding a value as high as 25%. Assuming a cell and tissue density of 1.05 g/cm$^3$, the expected overall physical density of QD-hMSCs should range from 1.40-2.00 g/cm$^3$. These densities are well above the threshold for detection of the μCT scanners.

7. EXAMPLE

Use of QDs to Track Labeled MSCS Non-Invasively In Vivo

The long term future of stem cell therapies will depend on the ability to track non-invasively. Both the core of the QD and the passivating shell contain metal ions (cadmium and zinc respectively). Metals are radiopaque, meaning they do not allow penetration of x-ray waves, and can therefore be imaged using x-ray technology. Traditional x-rays are too large to interfere with nano- or micro-scaled metals. However, since they are radiopaque, it may be possible to use micro computed tomography (μCT) scanning to image QDs in vivo.

7.1. Materials and Methods

Figure 7A:
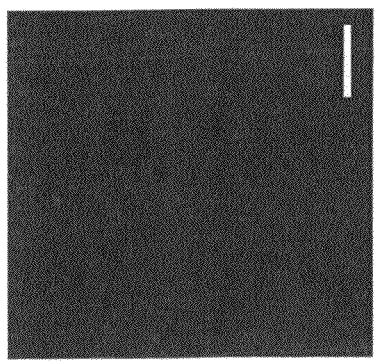

Preparation of cells for phantom. Qd-hMSCs were prepared as described above. After 24 hours, cells were washed and visualized to confirm QD loading (FIG. 7a). Cells from the QD-hMSC group and a separate control unloaded hMSC group were each trypisinized and centrifuged at 1000 g for 4 minutes in polypropylene tubes to prevent adhesion of cells to tube walls. The pellets were resuspended in MSCGM and the solution was then centrifuged at 1500 g for 5 minutes. Pellets were incubated at 37° C. overnight. After the incubation period and without breaking them up, pellets were gently washed in PBS and fixed in 4% paraformaldehyde for 2 hours.

Figure 7B:
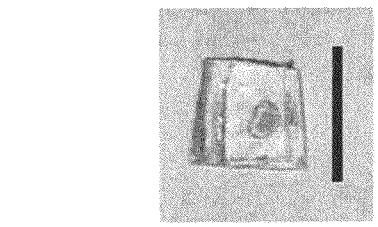
Figure 7C:
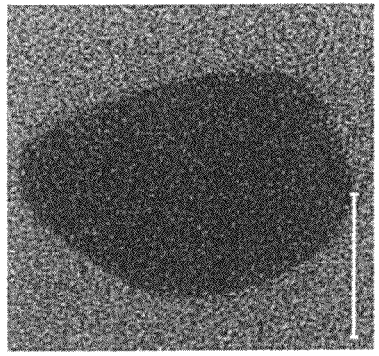

Creation of phantom mold. A curable siloxane compound was prepared by mixing vinylmethylpolysiloxane (GE silicones RTV615A, s.d.1.02 g/cm3) and vinyl MQ resin (GE silicones RTV615B, s.d.0.99 g/cm3) in a 10:1 ratio and stirring for 5 minutes. The mixture was then poured into two wells of a 4-well chamber slide to cover the bottom of the well and cured at 50° C. for 2 hours. The cell pellets were placed in each well and additional siloxane mixture was poured over the top to complete cover the pellets. The materials cured overnight at room temperature (FIG. 7b).

μCT scanning. High resolution (9 μm) μCT scanning (Scano Medical μCT 40, Basserdorf, Switzerland) was used to visualize cell pellets within the siloxane mold. Individual 2D images from the unloaded hMSC and QD-hMSC molds were visualized and densities in the cell pellet regions were measured from image intensities (12 and 16 images sampled respectively). A constrained 3D Gaussian filter was applied to reduce noise in the images ("support"=9, "sigma"=5). Cell pellet regions were segmented from the surrounding siloxane by thresholding (lower threshold=124, upper threshold = 1000). The 3D reconstruction was generated from the stack of binarized images.

Statistics. All data are listed as mean±standard deviation. Data sets were compared by a Student's t-test with $p<0.05$ considered significant.

7.2. Results

QDs are semiconductor nanoparticles comprised of a CdSe core and ZnS shell. Because of the very high densities of these materials (5.816 g/cm3 and 4.09 g/cm3 respectively), it was investigated whether QD-hMSCs could be imaged using micro-computed tomography (μCT) scanning. In order for QD-hMSCs to be detected within a block of tissue, two criteria must be satisfied: 1) the resolution of the CT scanner must be sensitive enough to detect single cells (mean diameter, 10 μm) and 2) the overall physical density of a QD-loaded hMSC must be at least 10% higher than the physical density of the surrounding tissue. Currently, micro CT (μCT) scanners are available with resolutions as low as 1 μm. The scanner used herein is a μCT scanner with 6 μm resolution which should satisfy the first criterion listed above.

As described above, after uptake by hMSCs, QDs exist within the cells in clusters with an average diameter of 0.75 μm. Prior to cell division the average cell contains approximately 200 of these QD clusters, as determined by fluorescence imaging. Since an individual cluster will occupy approximately 0.22 μm3 in the cell, the total volume of QDs in a given cell is roughly 44 μm3. An average hMSC has a volume of approximately 500 μm3. Therefore, based on these calculations, QDs occupy approximately 9% of the volume of the cell. This is a low-end estimate of the percent volume, with alternate calculations yielding a value as high as 25%. Assuming a cell and tissue density of 1.05 g/cm3, the expected overall physical density of QD-hMSCs should range from 1.14-2.00 g/cm3. These densities are well above the threshold for detection of the μCT scanner utilized.

Based on these findings, it is theoretically feasible for QD-hMSCs to be detected with μCT in both explanted tissue samples and in living animals.

Figure 7D:
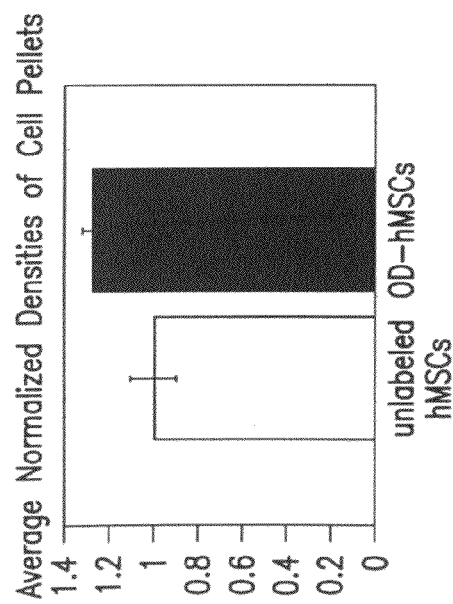
Figure 7E:
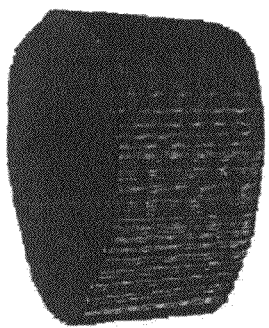

Both unloaded hMSC and QD-hMSC pellets were detectable within the siloxane mold (FIG. 7c) as areas of hypointensity. Regions of interest within the pellet area from sample images in each group were selected in order to measure densities (N=12 for unloaded hMSC, N=16 for QD-hMSC). Density measurements were normalized to the average density of the unloaded hMSC pellet. The values were 1.000±0.103 and 1.276±0.039 for unloaded and QD-hMSC pellets respectively (FIG. 7d). A 3-D reconstruction of the QD-hMSC pellet was generated from the stack of images (FIG. 7e).

The development of a tracking agent that can visualize delivered cells in vivo non-invasively with high resolution is highly desirable. Existing techniques for non-invasive tracking of stem cells include loading cells with radioactive substances like truncated thymidine kinase for positron emission tomography (PET) detection or radiometals for single photon emission computed tomography (SPECT). Concerns have arisen, however, over the uptake of the label by host tissue, endogenous tissue photon attenuation and high levels of label needed for detection. Another approach is the transfection of cells with the gene for luciferase; this allows cells to be visualized using bioluminescence. Major problems with this approach include the absorption and scatter of visible light and use of non-human genetic material. More commonly used for non-invasive cell tracking are radioopaque metals like iron (super paramagnetic iron oxide, SPIOs) and gadolinium. These materials are visualized using magnetic resonance imaging (MRI). For gadolinium, difficulties arise in loading the cells with sufficient concentrations to permit T1 contrast. Since high concentrations are needed, the dilution effects are pronounced as cells divide. SPIOs like ferridex are most frequently used, but conflicting studies exist on whether these particles interfere with chondrogenesis. If true, this would suggest they are not a "stealth" particle within the cell and could potentially interfere with other important physiologic functions. Further, should the technique be extended to clinical trials in humans, individuals with electronic pacemakers or implantable defibrillators would be excluded from the study. This would isolate a potentially needy patient population.

The present example demonstrates that passive QD loading of hMSCs yields cells that are labeled with sufficient QD clusters to theoretically permit detection via μCT. When pelleted and embedded in a siloxane mold, the labeled cells are detectable and found to be approximately 27% denser than unlabeled cells. This result is consistent with theoretical calculations. Based on these findings, it should be possible to detect a cluster of QD-hMSCs within heart tissue using μCT. To confirm feasibility QD-hMSCs will be injected into heart tissue and the sample will be scanned. Once done, non-invasive scanning can be tested in living animals. To synchronize the scanning with the heart beat the use of gating algorithms may be required. Scano Medical manufactures in vivo scanners for animals (vivaCT 40) and humans (XtremeCT) that have resolutions of 16 and 1001 μm respectively. These resolutions are acceptable (approximately single cell resolution for the animal scanner and 125-cell resolution for the human scanner) and superior to that attainable with SPIOs and MRI.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Throughout this application, various publications are referenced to by numbers. The disclosures of these publications in the entireties are hereby incorporated by reference into this application in order to more fully describe the state of the art to those skilled therein as of the date of the invention described and claimed herein.

REFERENCES

1. Klug, M. G., M. H. Soonpaa, G. Y. Koh, et al., *Genetically selected cardiomyocytes from differentiating embronic stem cells form stable intracardiac grafts*. J Clin Invest, 1996. 98(1): p. 216-24.
2. Yoon, Y. S., A. Wecker, L. Heyd, et al., *Clonally expanded novel multipotent stem cells from human bone marrow regenerate myocardium after myocardial infarction. J Clin Invest,* 2005. 115(2): p. 326-38.
3. Meyer, G. P., K. C. Wollert, J. Lotz, et al., *Intracoronary bone marrow cell transfer after myocardial infarction: eighteen months follow-up data from the randomized, controlled BOOST (BOne marrOw transfer to enhance ST-elevation infarct regeneration) trial.* Circulation, 2006. 113 (10): p. 1287-94.
4. Amado, L. C., A. P. Saliaris, K. H. Schuleri, et al., *Cardiac repair with intramyocardial injection of allogeneic mesenchymal stem cells after myocardial infarction. Proc Natl Acad Sci USA,* 2005.102(32): p. 11474-9.
5. Mangi, A. A., N. Noiseux, D. Kong, et al., *Mesenchymal stem cells modified with Akt prevent remodeling and restore performance of infarcted hearts*. Nat Med, 2003. 9(9): p. 1195-201.
6. Beltrami, A. P., K. Urbanek, J. Kajstura, et al., *Evidence that human cardiac myocytes divide after myocardial infarction*. N Engl J Med, 2001. 344(23): p. 1750-7.
7. Orlic, D., J. Kajstura, S. Chimenti, et al., *Bone marrow cells regenerate infarcted myocardium*. Nature, 2001. 410(6829): p. 701-5.
8. Murry, C. E., M. H. Soonpaa, H. Reinecke, et al., *Haematopoietic stem cells do not transdifferentiate into cardiac myocytes in myocardial infarcts*. Nature, 2004. 428(6983): p. 664-8.
9. Kehat, I., L. Khimovich, O. Caspi, et al., *Electromechanical integration of cardiomyocytes derived from human embryonic stem cells*. Nat Biotechnol, 2004. 22(10): p. 1282-9.
10. Potapova, I., A. Plotnikov, Z. Lu, et al., *Human mesenchymal stem cells as a gene delivery system to create cardiac pacemakers*. Circ Res, 2004. 94(7): p. 952-9.
11. Thomson, J. A., J. Itskovitz-Eldor, S. S. Shapiro, et al., *Embryonic stem cell lines derived from human blastocysts*. Science, 1998. 282(5391): p. 1145-7.
12. Laflamme, M. A. and C. E. Murry, *Regenerating the heart*. Nat Biotechnol, 2005. 23(7): p. 845-56.
13. Kraitchman, D. L., M. Tatsumi, W. D. Gilson, et al., *Dynamic imaging of allogeneic mesenchymal stem cells trafficking to myocardial infarction*. Circulation, 2005. 112 (10): p. 1451-61.
14. Bruchez, M., Jr., M. Moronne, P. Gin, et al., *Semiconductor nanocrystals as fluorescent biological labels*. Science, 1998. 281(5385): p. 2013-6.
15. Chan, W. C. and S, Nie, *Quantum dot bioconjugates for ultrasensitive nonisotopic detection*. Science, 1998. 281 (5385): p. 2016-8.
16. Isenberg, G. and U. Klockner, *Calcium tolerant ventricular myocytes prepared by preincubation in a "KB medium"*. Pflugers Arch, 1982. 395(1): p. 6-18.
17. Cordeiro, J. M., L. Greene, C. Heilmann, et al., *Transmural heterogeneity of calcium activity and mechanical function in the canine left ventricle*. Am J Physiol Heart Circ Physiol, 2004. 286(4): p. H1471-9.
18. Kochupura, P. V., E. U. Azeloglu, D. J. Kelly, et al., *Tissue-engineered myocardial patch derived from extracellular matrix provides regional mechanical function*. Circulation, 2005. 112(9 Suppl): p. 1144-9.
19. Derfus, A. M., Chan, W. C. W., and Bhatia, S. N., *Intracellular Delivery of Quantum Dots for Live Cell Labeling and Organelle Tracking. Advanced Materials,* 2004. 16(12): p. 961-966.
20. Dubertret, B., P. Skourides, D. J. Norris, et al., *In vivo imaging of quantum dots encapsulated in phospholipid micelles*. Science, 2002. 298(5599): p. 1759-62.
21. Voura, E. B., J. K. Jaiswal, H. Mattoussi, et al., Tracking metastatic tumor cell extravasation with quantum dot nanocrystals and fluorescence emission-scanning microscopy. Nat Med, 2004. 10(9): p. 993-8.
22. Gao, X., Y. Cui, R. M. Levenson, et al., *In vivo cancer targeting and imaging with semiconductor quantum dots*. Nat Biotechnol, 2004. 22(8): p. 969-76.
23. Hoshino, A., K. Hanaki, K. Suzuki, et al., Applications of T-lymphoma labeled with fluorescent quantum dots to cell tracing markers in mouse body. Biochem Biophys Res Commun, 2004. 314(1): p. 46-53.
24. Zhang, Y.a.H., N., *Intracellular uptake of CdSe-ZnS/polystyrene nanobeads*. Journal of Biomedical Materials Research Part B: Applied Biomaterials, 2005. 76B(1): p. 161-168.
25. So, M. K., C. Xu, A. M. Loening, et al., Self-illuminating quantum dot conjugates for in vivo imaging. Nat Biotechnol, 2006. 24(3): p. 339-43.
26. Silver, S.a.O., W., Photoactivation of Quantum Dot Fluorescence Following Endocytosis. Nano Letters, 2005. 5(7): p. 1445-1449.
27. Jaiswal, J. K., H. Mattoussi, J. M. Mauro, et al., *Long-term multiple color imaging of live cells using quantum dot bioconjugates*. Nat Biotechnol, 2003. 21(1): p. 47-51.
28. Piasek, A. and J. Thyberg, Effects of colchicine on endocytosis and cellular inactivation of horseradish peroxidase in cultured chondrocytes. J Cell Biol, 1979. 81(2): p. 426-37.
29. Valiunas, V., S. Doronin, L. Valiuniene, et al., *Human mesenchymal stem cells make cardiac connexins and form functional gap junctions*. J Physiol, 2004. 555(Pt 3): p. 617-26.
30. Page, E., J. Upshaw-Earley, G. E. Goings, et al., Fluid-phase endocytosis by in situ cardiac myocytes of rat atria. *Am J Physiol,* 1993. 265(4 Pt 1): p. C986-96.

31. Ballou, B., B. C. Lagerholm, L. A. Ernst, et al., *Noninvasive imaging of quantum dots in mice*. Bioconjug Chem, 2004.15(1): p. 79-86.
32. Britten, M. B., N. D. Abolmaali, B. Assmus, et al., *Infarct remodeling after intracoronary progenitor cell treatment in patients with acute myocardial infarction (TOPCARE-AMI): mechanistic insights from serial contrast-enhanced magnetic resonance imaginga*. Circulation, 2003. 108(18): p. 2212-8.
33. Wollert, K. C., G. P. Meyer, J. Lotz, et al., *Intracoronary autologous bone-marrow cell transfer after myocardial infarction: the BOOST randomised controlled clinical trial*. Lancet, 2004. 364(9429): p. 141-8.
34. Jackson, K. A., S. M. Majka, H. Wang, et al., *Regeneration of ischemic cardiac muscle and vascular endothelium by adult stem cells*. J Clin Invest, 2001. 107(11): p. 1395-402.
35. Kajstura, J., M. Rota, B. Whang, et al., *Bone marrow cells differentiate in cardiac cell lineages after infarction independently of cell fusion*. Circ Res, 2005. 96(1): p. 127-37.
36. Kraitchman, D. L., A. W. Heldman, E. Atalar, et al., *In vivo magnetic resonance imaging of mesenchymal stem cells in myocardial infarction*. Circulation, 2003. 107(18): p. 2290-3.
37. Thompson, R. B., S. M. Emani, B. H. Davis, et al., *Comparison of intracardiac cell transplantation: autologous skeletal myoblasts versus bone marrow cells*. Circulation, 2003. 108 Suppl 1: p. II264-71.
38. Dick, A. J., M. A. Guttman, V. K. Raman, et al., *Magnetic resonance fluoroscopy allows targeted delivery of mesenchymal stem cells to infarct borders in Swine*. Circulation, 2003. 108(23): p. 2899-904.
39. Barbash, I. M., P. Chouraqui, J. Baron, et al., *Systemic delivery of bone marrow-derived mesenchymal stem cells to the infarcted myocardium: feasibility, cell migration, and body distribution*. Circulation, 2003. 108(7): p. 863-8.
40. Hofmann, M., K. C. Wollert, G. P. Meyer, et al., *Monitoring of bone marrow cell homing into the infarcted human myocardium*. Circulation, 2005. 111(17): p. 2198-202.
41. Parish, C. R., *Fluorescent dyes for lymphocyte migration and proliferation studies*. Immunol Cell Biol, 1999. 77(6): p. 499-508.
42. Billinton, N. and A. W. Knight, *Seeing the wood through the trees: a review of techniques for distinguishing green-fluorescent protein from endogenous autofluorescence*. Anal Biochem, 2001. 291(2): p. 175-97.
43. Kim, S., Y. T. Lim, E. G. Soltesz, et al., *Near-infrared fluorescent type II quantum dots for sentinel lymph node mapping*. Nat Biotechnol, 2004. 22(1): p. 93-7.
44. Rieger, S., R. P. Kulkarni, D. Darcy, et al., *Quantum dots are powerful multipurpose vital labeling agents in zebrafish embryos*. Dev Dyn, 2005. 234(3): p. 670-81.
45. Hanaki, K., A. Momo, T. Oku, et al., *Semiconductor quantum dot/albumin complex is a long-life and highly photostable endosome marker*. Biochem Biophys Res Commun, 2003. 302(3): p. 496-501.
46. Hsieh, S. C., F. F. Wang, S. C. Hung, et al., *The internalized CdSe/ZnS quantum dots impair the chondrogenesis of bone marrow mesenchymal stem cells*. J Biomed Mater Res B Appl Biomater, 2006. 79(1): p. 95-101.
47. LeGrice, I., G. Sands, D. Hooks, et al., *Microscopic imaging of extended tissue volumes*. Clin Exp Pharmacol Physiol, 2004. 31(12): p. 902-5.
48. Frangioni, J. V. and R. J. Hajjar, *In vivo tracking of stem cells for clinical trials in cardiovascular disease*. Circulation, 2004. 110(21): p. 3378-83.

TABLE 1

```
% ABR 022806
% regQD.m
% This script takes as input a 2-D intensity image of QD+ cells (red
fluorescence) in a
% section of tissue (phase). Misregistration between successive images
is assumed to be
% purely translation. The user is prompted to select common points
from
% image to image, which are collected in the matrix DispMat
%clear all
numsect = 154;
dnes = [2 8 15 17 20 29 38 43 45 48 50 56 58 66 68 77 84 97 105 107 109
111 118 142 144 146 148 153];
%**************************** FILE NAME INPUTS
****************************
i = 98;
j = 1;
while i <= numsect
    if sum(i == dnes) ==0
    else
        i = i + 1
    end
    filename1 = ['3025_',num2str(i),'_(c2+c5).jpg'];
    I1 = imread(filename1);
%*********************** FIND NEW POINTS ***************************
imshow(I1);
[x,y] = ginput(1);
DispMat(j,:) = [x y i];
j = j + 1;
i = i + 1;
    if sum(i == dnes) ==0
    else
        i = i + 1;
    end
end;
% ABR 022806
% moveims.m
% This script takes as input a 2-D intensity image of QD+ cells (red
```

TABLE 1-continued

```
fluorescence) in a
% section of tissue (phase) and the DispMat output from the script
regQD.m.
% Images are registered with respect to the first image index in the
DispMat vector.
olddi = −142-268;
olddj = −62-228;
%is: 142, 268
%js: 62, 228
%is = [801 1830];
%js = [551 1850];
is = [801-olddj 1830-olddj];
js = [551-olddi 1850-olddi];
playmat = uint8(zeros(2630,2400,3));
%regim_1 = playmat;
%im1 = imread('3025_1_(c2+c5).jpg');
%regim_1(is(1):is(2),js(1):js(2),:) = im1;
%imwrite(regim_1,'regim_1.jpg');
%******************************* FILE NAME INPUTS
***************************
i = 2;
while i <= length(DispMat(:,3))
    filename2 = ['3025_',num2str(DispMat(i,3)),'_(c2+c5).jpg'];
    im2 = imread(filename2);
    regim = playmat;
    newpt = [DispMat(i,1,1) DispMat(i,2,1)];
    di = fix(newpt(1)−DispMat(1,1,1));
    dj = fix(newpt(2)−DispMat(1,2,1));
    if di >= is(1)
            di = is(1)−1;
    else
    end
    if dj >= js(1)
            dj = js(1)−1;
    else
    end
    regim(is(1)−dj:is(2)−dj, js(1)−di:js(2)−di,:) = im2;
    imwrite(regim, ['regim_',num2str(DispMat(i,3)),'.jpg']);
    clear im2, clear regim, clear newpt, clear trans*
    i = i + 1;
end
% ABR 022806
% cropims.m
is = [400 2300];
js = [200 2400];
%******************************* FILE NAME INPUTS
***************************
i = 1;
dnes = [2 8 15 17 20 29 38 43 45 48 50 56 58 66 68 77 84 97 105 107 109
111 118 142 144 146 148 153];
while i <= 154
    if sum(i == dnes) ==0
      else
        i = i + 1
    end
    filename = ['regim_',num2str(i),'.jpg'];
    im = imread(filename);
    newim = im(is(1):is(2), js(1):js(2),:);
    imwrite(newim, ['regim_crop_',num2str(i),'.jpg']);
    clear im, clear newim
    i = i + 1;
end
% ABR 033006
% QD3D_new.m for rat 3025
% This script takes as input a 2-D intensity image of QD+ cells (red
fluorescence) in a
% section of tissue (phase).  The QD+ regions are identified and a new
% matrix is prepared, identifying these features.  The dot images are
also
% translated to register with one another.  The input for this requires
% running regQD, moveims and cropims first.
DotMat = logical(zeros(380,440,154));
i = 1;
numsect = 126;
dnes = [2 8 15 17 20 29 38 43 45 48 50 56 58 66 68 77 84 97 105 107 109
111 118 142 144 146 148 153];
while i <= numsect
        if sum(i == dnes) ==0
          else
            i = i + 1;
```

TABLE 1-continued

```
    end
    filename = ['regim_crop_',num2str(i),'.jpg'];
    I1 = imread(filename);   % original image
%****************************** FIND QD+ REGIONS
********************************
    I1hsv = rgb2hsv(I1);           % convert RGB to HSV
    sat = I1hsv(:,:,2); val = I1hsv(:,:,3);
    valxsat = immultiply(sat, val);   % binarize value matrix
    %if sum(i == [80 86 87 88 89 92 93 94 95 96 99 98 100 116 117 120 121
122 124 125 126 127 128 132 133 134]) == 1
        threshval = 0.05;
    %else
    %    threshval = 0.025;
    %end
    dots = im2bw(valxsat, threshval);   % multiply binarized value
x sat
%************************* # PIXELS IN QD+ MATRIX
****************************
QDsum(i) = sum(dots(:));
%********************** ASSEMBLE 3D DOT MATRIX
******************************
DotMat(:,:,i) = logical(imresize(dots,.2));
clear I1*, clear dots, clear sat, clear val*
pack
i = i + 1;
end
%L = bwlabeln(DotMat);
%figure, p = patch(isosurface(smooth3(L),.8));
%reducepatch(p,.125)
%set(p,'facecolor',[1,0,0],'edgecolor','none');
%set(gca,'projection','perspective')
%box on
%daspect('default')
%lighting phong
%light('position',[1,1,1])
%light('position',[-1,-1,-1])
%light('position',[-1, 1,-1])
%light('position',[ 1,-1,-1])
figure, p = patch(isosurface(smooth3(L),.8));
set(p,'facecolor',[1,0,0],'edgecolor','none');
set(gca,'projection','perspective')
light('position',[1,1,1])
light('position',[-1,-1,-1])
light('position',[-1, 1,-1])
light('position',[ 1,-1,-1])
set(gca,'ZTickLabel',{'0.66';'';'1.06';'';'1.46';'';'1.86';''})
zlabel('mm','FontSize',24,'FontWeight','Bold')
set(gca,'XTick',[0 102.5010 205.0020 307.503 410.004])
set(gca,'XTickLabel',{'0';'0.5';'1.0';'1.5';'2.0'},'FontSize',24,'FontWeight','Bold')
set(gca,'YTick',[0 205.0020 410.004])
set(gca,'YTickLabel',{'0';'1.0';'2.0
'},'FontSize',24,'FontWeight','Bold')
xlabel('mm')
ylabel('mm')
```

TABLE 2

| outcome | Surface charge on dots | | | Additional conjugation | Emission wavelength (nm) | | | Method of loading | | | Media | | | Substrate | |
|---|---|---|---|---|---|---|---|---|---|---|---|---|---|---|---|
| | + | 0 | − | Streptavidin | 655 | 800 | 525 | Passive incubation | Qtracker | Electro-poration | Cambrex hMSC | DMEM | DMEM+ 10% FBS | Polystyrene | Glass |
| ✓ | • | | | | • | | | • | | | • | | • | • | |
| ✓ | • | | | • | • | | | • | | | • | | • | • | |
| X | • | | | | • | | | • | | | • | | • | • | |
| X | • | | | | • | | | • | | | | • | • | • | |
| X | • | | | | • | | | • | | | • | | | • | • |
| X | • | | | | • | | | | • | | • | | • | • | |
| X | • | | | | • | | | | | • | • | | • | • | |
| ✓ | • | | | • | | • | | • | | | • | | • | • | |
| X | | • | | • | | • | | • | | | • | | • | • | |
| X | | • | | • | | • | | • | | | • | | • | • | |
| X | • | | | | | • | | • | | | • | | • | • | |
| X | • | | | | | | • | • | | | • | | • | • | |

What is claimed:

1. A method for transfer of quantum dots into the cytosol of a cell, comprising passively contacting a target cell population of one or more isolated cells with negatively charged quantum dots for a time sufficient to permit transfer and accumulation of the quantum dots into the cytosol of the target cell.

2. The method of claim 1 wherein the quantum dots are composed of material selected from the group consisting of CdS, CdSe, CdTe, CdTe/ZnS or CdSe/ZnS.

3. The method of claim 1 wherein the negatively charged quantum dots are formed through conjugation of negatively charged groups onto the surface of the quantum dots.

4. The method of claim 1 wherein the quantum dots emit light at wavelengths of between 525-800 nanometers.

5. The method of claim 1 wherein the cell is a mesenchymal stem cell expressing a hyperpolarization-activated, cyclic nucleotide-gated ion channel.

6. The method of claim 1 wherein the target cell population, expresses a hyperpolarization-activated, cyclic nucleotide-gated ion channel that is a mutant or chimeric channel.

7. An isolated cell comprising negatively charged quantum dots that lack perinuclear aggregation, wherein the negatively charged quantum dots are from an exogenous source.

8. The cell of claim 7 wherein the quantum dots are composed of material selected from the group consisting of CdS, CdSe, CdTe, CdTe/ZnS or CdSe/ZnS.

9. The cell of claim 7 wherein the negatively charged quantum dots are formed through conjugation of negatively charged groups onto the surface of the quantum dots.

10. The cell of claim 7 wherein the quantum dots emit light at wavelengths of between 525-800 nanometers.

11. The cell of claim 7 wherein the cell is a mesenchymal stem cell expressing a hyperpolarization-activated, cyclic nucleotide-gated ion channel.

12. The cell of claim 7 wherein the cell expresses a hyperpolarization-activated, cyclic nucleotide-gated ion channel that is a mutant or chimeric channel.

13. A method for tracking the distribution and/or fate of quantum dot-labeled cells that have been administered to a subject afflicted with a cardiac rhythm disorder comprising (i) administering quantum dot-labeled cells, expressing hyperpolarization-activated, cyclic nucleotide-gated ion channel, to a region of the subject's heart, wherein expression of the hyperpolarization-activated, cyclic nucleotide-gated ion channel in said region of the heart is effective to induce a pacemaker current in the heart and (ii) detecting the distribution and/or fate of the quantum dot-labeled cells that have been administered to said subject.

14. The method of claim 13 wherein the quantum dots are composed of material selected from the group consisting of CdS, CdSe, CdTe, CdTe/ZnS or CdSe/ZnS.

15. The method of claim 13 wherein the negatively charged quantum dots are formed through conjugation of negatively charged groups onto the surface of the quantum dots.

16. The method of claim 13 wherein the quantum dots emit light at wavelengths of between 525-800 nanometers.

17. The method of claim 13 wherein the cell is a mesenchymal stem cell.

18. The method of claim 13 wherein the hyperpolarization-activated, cyclic nucleotide-gated ion channel is a mutant or chimeric channel.

19. The method of claim 13 wherein the cardiac rhythm disorder is selected from the group consisting of sinus node dysfunction, sinus bradycardia, marginal pacemaker function, sick sinus syndrome, tachyarrhythmia, sinus node reentry tachycardia, atrial tachycardia from an ectopic focus, atrial flutter, atrial fibrillation, brady arrhythmia, and cardiac failure.

20. The method of claim 19 wherein the quantum dot labeled cells are administered to the right or left atrial muscle, sinoatrial node, or atrioventricular junctional region of the subject's heart.

21. The method of claim 13 wherein the cardiac rhythm disorder to be treated is selected from the group consisting of conduction block, complete atrioventricular block, incomplete atrioventricular block, or bundle branch block.

22. The method of claim 21 wherein the quantum dot labeled cells are administered to the ventricular septum or free wall, atrioventricular junction, or bundle branch of the ventricle.

23. A bypass bridge comprising an isolated tract of gap junction-coupled quantum dot-labeled cells having a first end and a second end, both ends capable of being attached to two selected sites in a heart so as to allow the conduction of an electrical signal across the tract between the two sites, wherein the cells functionally express a sodium channel.

24. The bridge of claim 23 comprising quantum dot labeled cells on an extracellular matrix.

25. A method of making a bypass bridge for implantation in a heart, which is composed of quantum dot-labeled cells comprising: (a) transfecting a cell with, and functionally expressing therein, a nucleic acid encoding a sodium channel; and (b) growing the transfected cells into a tract of cells having a first and a second end capable of being attached to two selected sites in the heart, wherein the cells are physically interconnected via electrically conductive gap junctions.

26. The method of claim 25 wherein the cell is a mesenchymal stem cell.

27. A method of assessing the fate and distribution of quantum dot-labeled cells implanted as a bypass bridge in a heart comprising: (a) making a bypass bridge utilizing quantum dot-labeled cells; (b) selecting a first and a second site in the heart; (c) attaching the first end of the tract to the first site and the second end of the tract to the second site; so as to thereby implant a bypass bridge in the heart that allows the conduction of an electrical signal across the tract between the two sites, and (d) assessing the fate and distribution of the quantum dot-labeled cells.

28. A method of assessing the fate and distribution of quantum dot-labeled cells for use in treating a disorder associated with an impaired conduction in a subject's heart comprising: (a) transfecting a cell with a nucleic acid encoding a sodium channel, wherein the cell functionally expresses the sodium channel (b) loading the cells with quantum dots either before or after transfection; (c) growing the transfected cells into a tract of cells having a first end and a second end, wherein the cells are physically interconnected via electrically conductive gap junctions; (d) selecting a first site and a second site in the heart between which sites conduction is impaired; (e) attaching the first end of the tract to the first site and the second end of the tract to the second site; so as to allow the conduction of an electrical signal across the tract between the two sites and thereby treat the subject and (f) detecting the fate and distribution of quantum dot-labeled cells.

29. A method of assessing the fate and/or distribution of quantum dot labeled cells for treating a disorder associated with an impaired conduction and impaired sinus node activity in a subject's heart comprising: (a) transfecting a quantum dot-labeled cells with at least one nucleic acid encoding a sodium channel and a pacemaker ion channel, wherein the quantum dot-labeled cell functionally expresses the sodium channel and the pacemaker ion channel; (b) loading cells with quantum dots either before or after transfection; (c) growing the transfected quantum dot-labeled cell into a tract of cells having a first end and a second end, wherein the cells are physically interconnected via electrically conductive gap junctions; (d) selecting a first site in the left atrium of the heart and a second site, between which sites conduction is impaired; and (e) attaching the first end of the tract to the first site and the second end of the tract to the second site; so as to allow the propagation of an electrical signal generated by the sinus node and/or tract of cells between the two sites and thereby treat the subject.

30. A tandem pacemaker system comprising (i) an electronic pacemaker, and (ii) a biological pacemaker, wherein the biological pacemaker comprises an isolated implantable quantum dot-labeled cell, wherein said cell functionally expresses a HCN and wherein the expressed chimeric HCN channel generates an effective pacemaker current.

31. A tandem pacemaker system comprising (i) an electronic pacemaker, and (ii) a bypass bridge comprising a strip of isolated gap junction-coupled quantum dot-labeled cells having a first end and a second end, both ends capable of being attached to two selected sites in a heart, so as to allow the transmission of an electrical signal across the tract between the two sites in the heart.

* * * * *

UNITED STATES PATENT AND TRADEMARK OFFICE
CERTIFICATE OF CORRECTION

PATENT NO. : 8,170,665 B2  Page 1 of 1
APPLICATION NO. : 12/077970
DATED : May 1, 2012
INVENTOR(S) : Cohen et al.

It is certified that error appears in the above-identified patent and that said Letters Patent is hereby corrected as shown below:

Column 1, Lines 12 – 14, please replace the whole paragraph with the following:

STATEMENT OF GOVERNMENTAL INTEREST
This invention was made with government support under Contract Nos. HL28958 and HL-67101 awarded by Department of Health and Human Services and the National Institutes of Health. The government has certain rights in the invention.

Signed and Sealed this
Sixth Day of November, 2012

David J. Kappos
*Director of the United States Patent and Trademark Office*